(12) United States Patent
Vervaet et al.

(10) Patent No.: US 11,065,207 B2
(45) Date of Patent: *Jul. 20, 2021

(54) ORAL DOSAGE FORM

(71) Applicant: Universiteit Gent, Ghent (BE)

(72) Inventors: Chris Vervaet, Kachtem (BE); Jean Paul Remon, Melle (BE); Glenn Verstraete, Rollegem-Kapelle (BE)

(73) Assignee: Universiteit Gent, Ghent (BE)

( * ) Notice: Subject to any disclaimer, the term of this patent is extended or adjusted under 35 U.S.C. 154(b) by 331 days.

This patent is subject to a terminal disclaimer.

(21) Appl. No.: 16/087,835

(22) PCT Filed: Mar. 24, 2017

(86) PCT No.: PCT/EP2017/057063
§ 371 (c)(1),
(2) Date: Sep. 24, 2018

(87) PCT Pub. No.: WO2017/162852
PCT Pub. Date: Sep. 28, 2017

(65) Prior Publication Data
US 2020/0297647 A1    Sep. 24, 2020

(30) Foreign Application Priority Data
Mar. 25, 2016    (EP) .................... 16162491

(51) Int. Cl.
*A61K 9/48*    (2006.01)
*A61K 9/20*    (2006.01)
(Continued)

(52) U.S. Cl.
CPC .......... *A61K 9/4866* (2013.01); *A61K 9/1635* (2013.01); *A61K 9/1652* (2013.01);
(Continued)

(58) Field of Classification Search
None
See application file for complete search history.

(56) References Cited

U.S. PATENT DOCUMENTS 6,558,704 B1    5/2003    Bartholomaeus et al.
7,351,429 B1 *    4/2008    Ohyama ................. A61P 13/02
                                            424/465
2010/0062062 A1    3/2010    McMillan et al.

FOREIGN PATENT DOCUMENTS

EP    0 169 382 A2    6/1985
EP    0 468 247 A1    7/1991
(Continued)

OTHER PUBLICATIONS

Saxena (Polyvinyl alcohol, Chemical and Technical Assessment, FAO 2004) . (Year: 2004).*
(Continued)

*Primary Examiner* — Melissa S Mercier
(74) *Attorney, Agent, or Firm* — Dinsmore & Shohl, LLP

(57) ABSTRACT

The present invention in general relates to a pharmaceutical dosage form comprising one or more granules, and a method for manufacturing thereof. The granules of the dosage form are prepared via the extrusion/spheronization technique using partially hydrolysed polyvinyl alcohol. These granules have the advantage that a high drug load can be contained therein.

12 Claims, 8 Drawing Sheets

(51) Int. Cl.
   A61K 9/16    (2006.01)
   A61K 31/155  (2006.01)
   A61K 45/00   (2006.01)
(52) U.S. Cl.
   CPC .......... *A61K 9/2027* (2013.01); *A61K 9/2054*
           (2013.01); *A61K 31/155* (2013.01); *A61K*
                                    *45/05* (2013.01)

(56) References Cited

FOREIGN PATENT DOCUMENTS

| EP | 1 974 724 A2 | 9/2001 |
|---|---|---|
| WO | 2007143158 A2 | 12/2007 |
| WO | 2015/155307 A1 | 10/2015 |

OTHER PUBLICATIONS

Keleb et al. (Cold Extrusion as a continuous single-step granulation and tableting processing, European Journal of Pharmaceutics and Biopharmaceutics 52 (2001) 359-368). (Year: 2001).*

De Araujo-Junior, et al., Preparation of pellets containing Pothomorphe umbellata extracts by extrusion-spheronization: improvement of 4-nerolidylcatechol photostability, Brazilian Journal of Pharmacognosy, Jan./Feb. 2013, vol. 23, No. 1, pp. 169-173, Brazil.

Basit, et al., Formulation of Ranitidine Pellets by Extrusion-Spheronization with Little or No Microcrystalline Cellulose, Pharmaceutical Development and Technology, 1999, vol. 4, Issue 4, pp. 499-505, United Kingdom.

Chatchawalsaisin, et al., The preparation by extrusion/spheronization and the properties of pellets containing drugs, microcrystalline cellulose and glyceryl monostearate, European Journal of Pharmaceutical Sciences, 2005, vol. 24, pp. 35-48, United Kingdom.

Chatlapalli, et al., Physical characterization of HPMC and HEC and investigation of their use as pelletization aids, International Journal of Pharmaceutics, 1998, vol. 161, pp. 179-193, USA.

De Jaeghere, et al., Hot-melt extrusion of polyvinyl alcohol for oral immediate release applications, International Journal of Pharmaceutics, 2015, vol. 492, pp. 1-9, United Kingdom.

Dukic-Ott, et al., Production of pellets via extrusion-spheronisation without the incorporation of microcrystalline cellulose: A critical review, European Journal of Pharmaceutics and Biopharmaceutics, 2009, vol. 7, pp. 38-46, United Kingdom.

Fielden, et al., Thermal Studies on the Interaction of Water and Microcrystalline Cellulose, Journal of Pharmaceutics, Jan. 21, 1988, vol. 40., pp. 674-678, United Kingdom.

Garekani, et al., Preparation and characterization and release properties of Eudragit RS based ibuprofen pellets prepared by extrusion spheronization: effect of binder type and concentration, Drug Development and Industrial Pharmacy, Taylor & Francis Group, ISSN: 0363-9045, http://doi.org/10.3109/03639045.20012.707207; 2013, vol. 39, No. 8, pp. 1238-1246, USA.

Koester, et al., New Insights into the Pelletization Mechanism by Extrusion/Spheronization, American Association of Pharmaceutical Scientists, Dec. 2010, vol. 11, No. 4, pp. 1549-1551, USA.

Kranz, et al., Drug release from MCC- and carrageenan-based pellets: Experiment and theory, European Journal of Pharmaceutics and Biopharmaceutics, 2009, vol. 73, pp. 302-309, United Kingdom.

Law, et al. Use of hydrophilic polymers with microcrystalline cellulose to improve extrusion-spheronization, European Journal of Pharmaceutics and Biopharmaceutics, 1998, vol. 45, pp. 57-65, United Kingdom.

Lustig-Gustafsson, et al., The influence of water content and drug solubility on the formulation of pellets by extrusion and spheronisation, European Journal of Pharmaceutical Sciences, 1999, vol. 8, pp. 147-152, United Kingdom.

Mallipeddi, et al., Use of coarse ethylcellulose and PEO in beads produced by extrusion-spheronization, International Journal of Pharmaceutics, 2010, vol. 385, pp. 53-65, United Kingdom.

O'Connor, et al., Spheronization II: Drug Release From Drug-Diluent Mixtures, Drug Development and Industrial Pharmacy, 1985, vol. 11, No. 9 & 10, pp. 1837-1857, USA.

Verheyen, et al., Use of crospovidone as pelletization aid as alternative to microcrystalline cellulose: effects on pellet properties, Drug Development and Industrial Pharmacy, ISSN: 0363-9045, http://doi.org/10.3109/03639040902902401; 2009, vol. 35, No. 11, pp. 1325-1332, Germany.

Vertommen, et al., The Influence of Five Selected Processing and Formulation Variable on the Particle Size, Particle Size Distribution, and Friability of Pellets Produced in a Rotary Processor, Drug Development and Industrial Pharmacy, 1997, vol. 23, No. 1, pp. 39-46, Belgium.

Wlosnewski, et al., Effect of drying technique and disintegrant on physical properties and drug release behavior of microcrystalline cellulose-based pellets prepared by extrusion/spheronization, Chemical Engineering Research and Design, 2010, vol. 88, pp. 100-108, Thailand.

European Search Report pertaining to EP Application No. 16162491.1, 10 pages, dated Jun. 6, 2016.

International Search Report and Written Opinion pertaining to International Application No. PCT/EP2017/057063, 16 pages, dated Jun. 17, 2017.

Chris Brough et al., Use of Polyvinyl Alcohol as a Solubility-Enhancing Polymer for Poorly Water Soluble Drug Delivery (Part 1), American Associate of Pharmaceutical Scientists, vol. 17, No. 1, Feb. 2016.

* cited by examiner

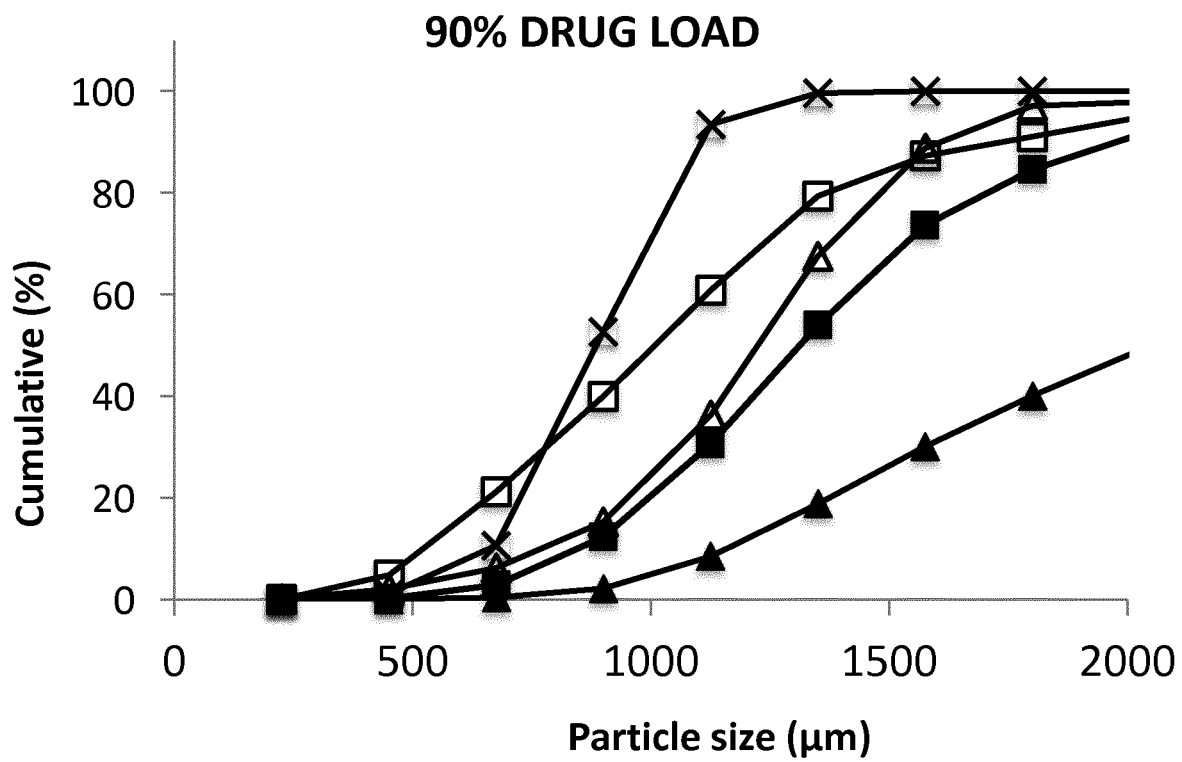
FIGURE 1 - continued aspect ratio sphericity

A.

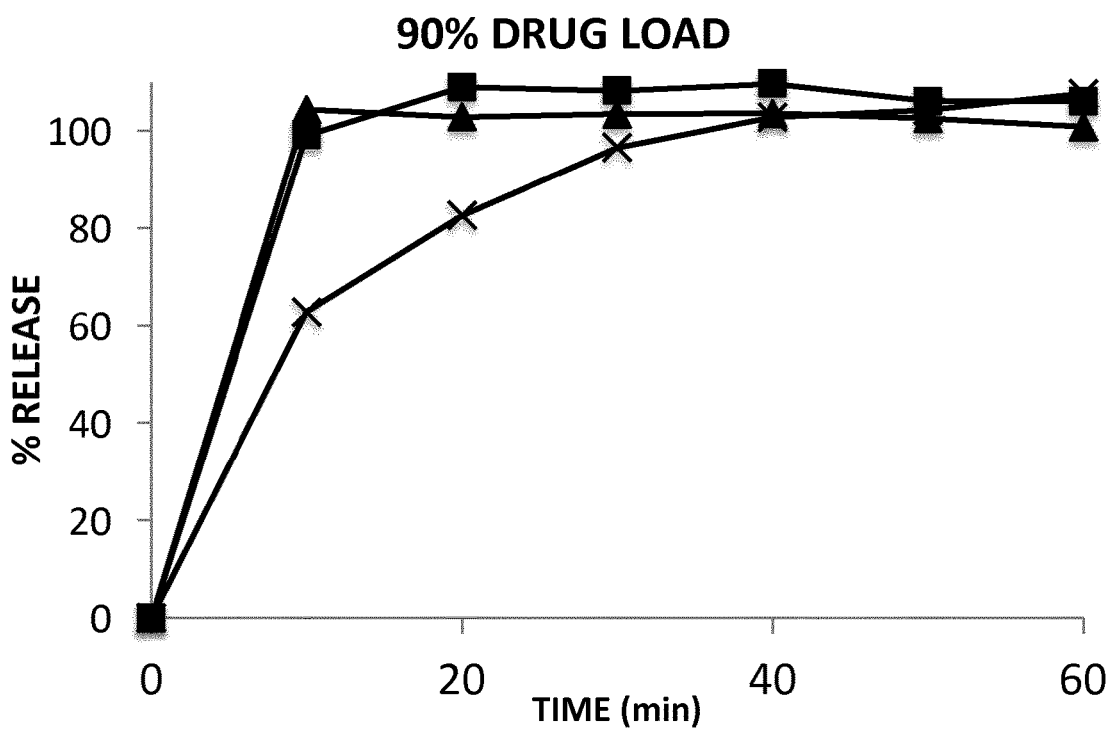
B.
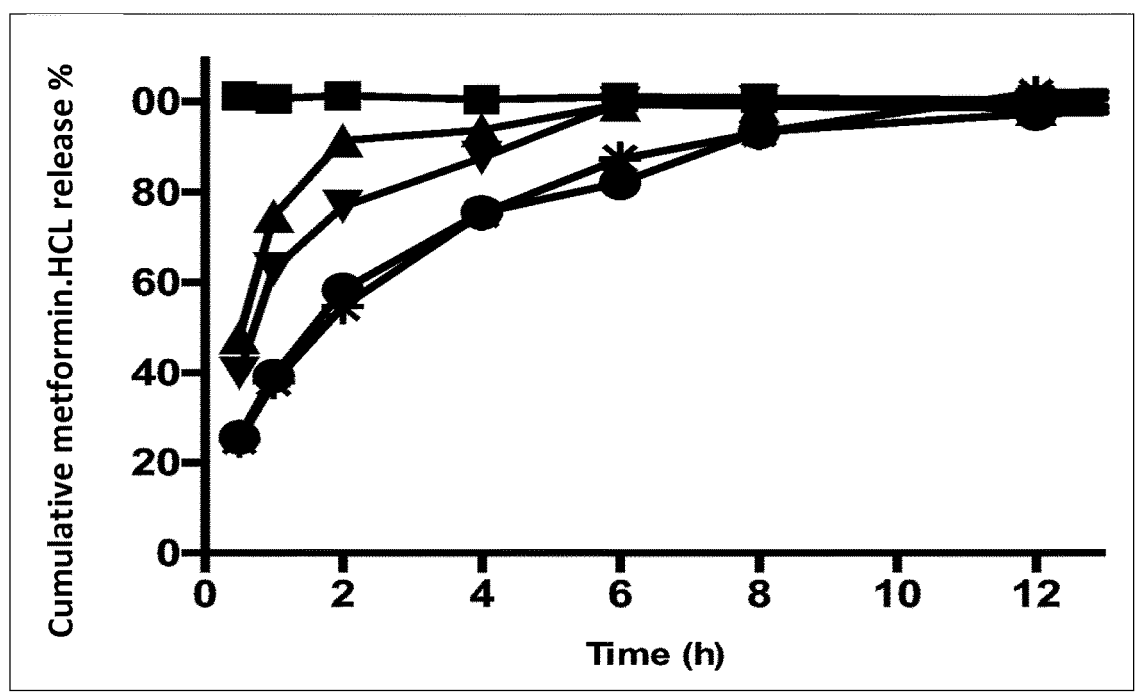
FIGURE 3 – continued

ORAL DOSAGE FORM

FIELD OF THE INVENTION

The present invention in general relates to a pharmaceutical dosage form comprising one or more granules, and a method for manufacturing thereof. The granules of the dosage form are prepared via the extrusion/spheronization technique using partially hydrolysed polyvinyl alcohol. These granules have the advantage that a high drug load can be contained therein.

BACKGROUND TO THE INVENTION

Multiparticulate drug delivery systems (e.g. pellets/granules) are becoming more important due to their distinct advantages compared to single unit systems, such as reproducible and generally short gastric/intestinal residence time, flexibility to blend pellets with different compositions or release patterns (personalized medicines), and decreased risk of dose dumping (Dukic-Ott et al., 2007). Pellets, which are defined in pharmaceutical industry as small (between 0.5 and 2.00 mm), free-flowing, spherical particles, can be obtained by solution or suspension layering of cores, powder layering, spray congealing, melt spheronisation or extrusion/spheronisation (Lustig-Gustafsson et al., 1999). Extrusion/spheronisation is the most popular pelletisation technique and is suitable to produce pellets with extended release profile. However, this technique requires the production of a cohesive wet mass which does not adhere to the extruder and retains some degree of rigidity. Furthermore, the extrudates need to be brittle enough to break into smaller extrudates and contain some degree of plasticity to deform into spheres (Swarbrick, 2006). As most drug molecules do not exhibit these characteristics, microcrystalline cellulose (MCC) is conventionally used as excipient to obtain formulations with sufficient rigidity, plasticity and water absorbing capacity. However, the use of MCC has some disadvantages, such as higher batch-to-batch variability due to its natural origin, increased disintegration time, incompatibility with certain drug molecules (Basit et al., 1999). Furthermore, the drug load in MCC based pellets is limited (Mallipeddi et al., 2010), which restricted the use of those pellets in fixed dose combinations, whereby two or more drugs are combined inside the pellets. Combination drug therapy is recommended for elderly and long-term care patients in order to facilitate patient compliance (Raffa, 2001). Therefore, several alternatives such as biopolymers (i.e. starch, chitosan) or synthetic polymers (i.e. hydroxypropyl methylcellulose, polyethylene oxide) are proposed in order to decrease MCC concentration in the pellets. However, these materials have inferior properties (e.g., less water holding capacity, ionic polymers require granulation liquid with a specific pH) for extrusion/spheronisation, compared to MCC (Dukic-Ott et al., 2009).

In an attempt to provide a solution to the above mentioned problems with the currently used extrusion aids (e.g. MCC), the present invention has demonstrated for the first time that inclusion of partially hydrolyzed polyvinyl alcohol in granules allows to manufacture oral dosage forms with a high drug load.

Partially hydrolysed polyvinyl alcohol (PVOH; PVA) is a water-soluble synthetic polymer produced by polymerisation of vinyl acetate followed by partial hydrolysis and therefore several grades with different degree of polymerization and hydrolysis are available. Pharmaceutical grades PVOH are mainly partially hydrolysed and are currently used in pharmaceutical applications as stabilizing or viscosity-increasing agent, and are often used in the preparation of coating layers of pharmaceutical pellets or tablets (EP0468247, US2010062062, Araujo-Junior et al., 2012). Partially hydrolysed PVOH was also evaluated for processing in hot melt extrusion but here again only formulations with low drug load could be produced (De Jaeg here W et al., 2015).

SUMMARY OF THE INVENTION

The present invention thus provides granules that can be utilized in a multiparticulate dosage form that provides rapid, sustain end and/or controlled release of a drug from the dosage form, particularly when the dosage form is orally administered. The dosage form has the advantage that a high drug load can be contained.

The present invention relates to a pharmaceutical dosage form or formulation comprising one or more granules having a core and optionally a coat; wherein said core comprises at least one active agent, partially hydrolyzed polyvinylalcohol (PVOH) and a diluent, in particular microcrystalline cellulose (MCC). In particular, the granule is an extrudate. Even more in particular, the granule is prepared via an extrusion and/or spheronization process, hence in said embodiment the dosage form comprises one or more extruded and/or spheronized granules. The partially hydrolyzed PVOH is a copolymer of vinyl alcohol and vinyl acetate, having a degree of hydrolysis between 30 and 95%, more particular between 70 and 95% and even more particular between about 70 and about 90%. In a specific embodiment, the partially hydrolyzed PVOH is present at an amount varying between and about 1 and 20% by weight of the core of the particle; more in particular between about 1 and 15% by weight of the core of the particle. The diluent (specifically the MCC) is generally present at an amount of between and about 1 and 30% by weight of the core of the particle. Furthermore, the active agent is present at an amount of at least 50% by weight of the core of the particle. Typically, the granule is substantially spherical and has a diameter in the range of about 0.3 to about 3 mm.

In a further embodiment, the dosage form of the present invention is a multiparticulate dosage form or composition (e.g. a tablet, capsule or unit-dose), formulated as an oral dosage form and especially suitable for the immediate, controlled and/or sustained release of one, two or more active agents. Optionally, a pharmaceutically acceptable excipient, a further diluent and/or carrier can be added to the composition.

In a further embodiment, the granule further comprises at least one coating layer, talc layer and/or taste-masking layer, in particular a coating layer comprising a suitable polymer, such as e.g. an acrylic-based polymer.

The present invention further encompasses the dosage form or composition of the present invention for use as a veterinary or human medicine and a method for the release of one or more active agents comprising orally administering to a subject said dosage form or composition.

A particular method of preparing a granule in accordance with the present invention comprises the steps of:
  mixing an active agent, partially hydrolyzed polyvinyl alcohol and a diluent;
  wetting the mixture;
  extruding the wet mixture to obtain an extrudate;
  spheronizing the extrudate to obtain a plurality of substantially spherical granules; and
  drying the granules.

PVOH can be added as a dry powder or as an aqueous solution. Optionally, the method further comprises a coating step (after the drying step). The invention also comprises the granules obtained by the method as described herein.

DETAILED DESCRIPTION OF THE INVENTION

Figure 1:
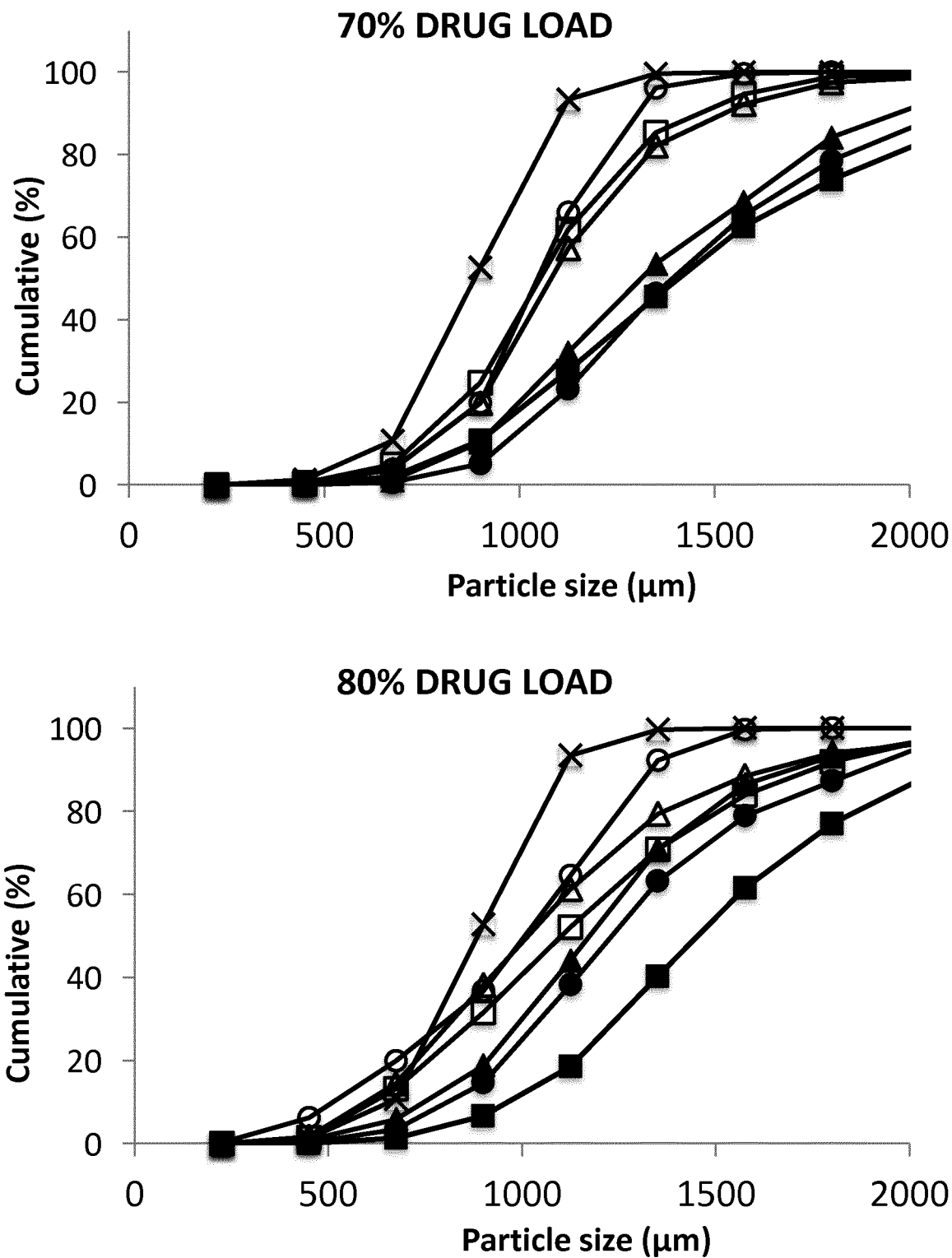
FIG. 1: Particle size distributions (mean±standard deviation, n=3) of formulations containing 70% drug (Form. 2 (■), 3 (▲), 4 (●)), 80% drug (Form. 7 (■), 8 (▲), 9 (●)) or 90% drug (Form. 14 (■), 15 (▲)) and PVOH. PVOH was added either in dry powder form (closed symbol) or as aqueous dispersion (open symbol). MCC pellets were used as reference (X).

As used herein, the singular forms "a", "an", and "the" include plural referents unless the context clearly dictates otherwise. The terms "comprising", "comprises" and "comprised of" as used herein are synonymous with "including", "includes" or "containing", "contains", and are inclusive or open-ended and do not exclude additional, non-recited members, elements or method steps. The term "about" as used herein when referring to a measurable value such as a parameter, an amount, a temporal duration, and the like, is meant to encompass variations of +/−10% or less, preferably +1-5% or less, more preferably +/−1% or less of and from the specified value, insofar such variations are appropriate to perform in the disclosed invention. It is to be understood that the value to which the modifier "about" refers is itself also specifically, and preferably, disclosed. Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any >3, >4, >5, >6 or >7 etc. of said members, and up to all said members. All references, and teachings specifically referred to, cited in the present specification are hereby incorporated by reference in their entirety. Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. Reference throughout this specification to "one embodiment" or "an embodiment" means that a particular feature, structure or characteristic described in connection with the embodiment is included in at least one embodiment of the present invention.

The present invention provides a wet mass formulation with the desired characteristics for both extrusion and spheronization; in particular for cold extrusion (i.e. extrusion at room temperature or near room temperature; typically between about 10° C. and about 40 or 50° C.). More specific, the mass is plastic enough to be extruded through the fine pores of an extruder and does not crumble apart. At the same time, the extrudates obtained from the formulation are sufficiently brittle so that they may be broken apart and spheronized in a spheronizer. Hence there is an optimal balance between the two desired properties i.e. plasticity and brittleness.

The present invention has demonstrated for the first time that inclusion of polyvinyl alcohol allows manufacturing granules, more particular spherical granules such as pellets, using formulations with a high drug load. Moreover, said granules provide the characteristics that are desirable for the oral administration of drugs. It was further demonstrated that these formulations have the desired balance of plasticity and brittleness and are hence particularly useful in manufacturing granules via extrusion and spheronization; in particular via cold extrusion.

In one embodiment, the present invention provides a spherical particle comprising (a combination of) at least one active ingredient, partially hydrolyzed polyvinylalcohol (PVOH) and a diluent, preferably microcrystalline cellulose (MCC). In particular, the at least one active ingredient, partially hydrolyzed polyvinylalcohol (PVOH) and diluent are present in the core of the particle.

The term "granules" as used herein means free-flowing particles with a narrow size distribution, typically varying between 0.5 and 3 mm in size for pharmaceutical applications. Spherical granules are also referred to as pellets. Typically they are formed as a result of a pelletization process resulting into small, free-flowing, spherical or semi-spherical units. Pellets, being multiple unit-dosage forms, are widely used as they offer both manufacturing and therapeutic advantages over single-unit solid dosage forms. There are different techniques applicable for the production of pellets in pharmaceutical industries. In the present invention, the granules/pellets have a diameter preferably ranging from about 0.3 to about 3.0 mm, more preferably from about 0.5 to 2.0 mm, even more preferably from 0.7 to 1.5 mm, and most preferably from 0.8 to 1.2 mm.

"Partially hydrolyzed polyvinyl alcohol (PVOH; PVA; general formula [CH$_2$CH(OH)]$_n$)", used for pharmaceutical applications, is a copolymer of vinyl acetate (CH$_3$CO$_2$CHCH$_2$) and vinyl alcohol (CH$_2$CHOH). Polyvinyl acetate is a water-insoluble polymer which is obtained by polymerization of vinyl acetate. This polymer is used for the production of polyvinyl alcohol by hydrolysis or alcoholysis to remove the acetyl groups from polyvinyl acetate. This removal of acetyl groups may be carried out to partial completion so as to give a product which is a copolymer of vinyl alcohol and vinyl acetate. If vinyl alcohol predominates, but there is still a substantial quantity of vinyl acetate present, such a copolymer is soluble in cold water and is frequently referred to as "partially hydrolyzed" polyvinyl alcohol. The residual vinyl acetate content is typically about 11 wt % corresponding to about 12 mol %. If the reaction is taken further, close to completion, the crystallinity of the polyvinyl alcohol increases and the solubility in cold water decreases very markedly. Material of this type is referred to as "fully hydrolyzed" polyvinyl alcohol. Its content of residual vinyl acetate is typically no greater than 3 mol %.

Several polyvinyl alcohol grades are commercially available. They mainly differ in molecular weight and residual content of acetyl groups (i.e. degree of hydrolysis). Different commercially available PVOH grades are listed herein and can be used in the embodiments of the present invention.

| PVOH grade | Mw | Degree of hydrolysis (mol %) | Pharmaceutical grade? |
|---|---|---|---|
| Partially hydrolysed | | | |
| PVA 5-05 | 38,000 | 72.5-74.5 | no |
| PVA4-88 | 31,000 | 86.7-88.7 | yes |
| PVA5-88 | 39,000 | 86.7-88.7 | yes |
| PVA8-88 | 67,000 | 86.7-88.7 | yes |
| PVA18-88 | 130,000 | 86.7-88.7 | yes |
| PVA26-88 | 183,000 | 86.7-88.7 | yes |
| PVA40-88 | 205,000 | 86.7-88.7 | yes |
| Fully hydrolysed | | | |
| PVA4-98 | 27,000 | 99.0-99.8 | yes |
| PVA28-99 | 145,000 | 99.0-99.8 | Limited to JPE |

Fully hydrolysed PVOH grades are only slightly soluble in water. Therefore, the ability to add enough PVOH via the wet addition method is limited, making it impossible to achieve high drug loaded pellets with good quality attributes. Partially hydrolysed polyvinyl alcohol are completely soluble. Based on their high aqueous solubility, these grades were evaluated for their potency as a pelletisation aid (via liquid addition method).

The preferred soluble polymer is partially hydrolyzed polyvinyl alcohol. As already mentioned above this is a copolymer of polyvinyl alcohol with vinyl acetate. Generally these copolymers are hydrolyzed to an extent between 30 and 95 mol %, more commonly between 50 and 95 mol %, in particular between 60 and 95 mol %, even more in particular between 70 and 95 mol %, and most particular between about 70 and 90 mol %. Thus, the mole ratio of vinyl alcohol to vinyl acetate lies between 30:70 and 95:5, preferably between 40:60 and 90:10. Partially hydrolyzed polyvinyl alcohol is fully biodegradable. The skilled person will be aware that depending on the water content and the type and/or concentration of the API in the core of the granule, the amount of PVOH can vary. In a specific embodiment, the granule core comprises up to 30 wt. % of partially hydrolyzed PVOH, preferably up to 20 wt. %, more preferably up to 14 wt. %, even more preferably up to and including 2, 3, 4, 5, 6, 7, 8, 9, 10, 11, 12 or 13 wt. %, and more in particular about and between 0.5 and 20 wt. % of PVOH, preferably about and between 1 and 15 wt. % of PVOH, more preferably about and between 1 and 10 wt. % of PVOH, including all values in between.

As used herein, a "diluent" is a diluting agent, which is water insoluble, and has a large water absorption and retention capacity. Suitable diluents useful in the present invention include biopolymers, such as powered cellulose, starch (derivatives), chitosan, K-carrageenam, pectinic acid; (semi-)synthetic polymers, such as hydroxypropyl methylcellulose, hydroxyethyl cellulose, polyethylene oxide, cross-linked polyvinylpyrrolidone; and other materials such as glyceryl monostearate. In a preferred embodiment, the diluent is microcrystalline cellulose. "Microcrystalline cellulose" (MCC), in particular a pharmaceutical grade thereof, is well known in the art of pharmaceutical industry for its high surface porosity and its outstanding capillary character. It is available from a variety of commercial sources, e.g. Avicel® PH101 (commercially available from FMC Corporation, Philadelphia, Pa.), Emcocel® (Mendell), Vivocel® (JRS), and the like. Microcrystalline cellulose is a partially purified depolymerized form of cellulose and is obtained by treating pulps derived from fibrous plant material with mineral acid. The acid preferentially attacks the less ordered or amorphous regions of the cellulose polymer chain, thereby exposing and freeing the crystalline sites which form cellulose crystallite aggregates. The reaction mixture is washed to remove the degraded byproducts, the resulting wetcake is freed of water and the dried cellulose crystallite aggregates, or more commonly MCC, recovered. MCC is a white, odorless, tasteless, relatively free-flowing powder, insoluble in water, organic solvents, dilute alkalies and dilute acids. In a specific embodiment, the core of the granule of the present invention may comprise up to 40 wt. % of a diluent, in particular MCC, more specific about and between 0 and 40 wt. % of diluent, even more specific between 0.5 and 35 wt. %, and preferably between 1 and 30 wt. % diluent, more preferred between 5 and 25 wt. % and even more preferred between 5 and 20 wt. % diluent, including all values in between.

The ratio PVOH/MCC within the core of the granule generally depends on the concentration of the API (and optionally the water content) and can readily be determined by the skilled person. In a particular embodiment, the PVOH/MCC ratio in the core of the granule or pellet is 50/50, but preferably about or within the range 45/55 and 1/99, such as e.g. 40/60, 30/70, 20/80, 10/90 or 5/95, including the ratios in between. In general, the ratio PVOH/MCC will increase with increasing drug concentration in the granule.

In a specific embodiment, the pharmaceutical dosage form or more specifically the core of the granules of the present invention do not contain any plasticizer, such as but not limited to polyethylene glycol, glycerol and sorbitol.

The active ingredient(s), partially hydrolyzed polyvinyl-alcohol (PVOH) and the diluent, such as MCC, form the "core" of the pellet. The granules may be used as they are, or optionally, a coating material may be applied, preferably by means of the film-coating process, to the granules. The granules may be coated for one or more functional purposes which include, without limitation, for further controlling the release properties of the active agent, for taste masking, for imparting resistance to gastric fluid, and to improve its shelf-life. Film coating involves the deposition, usually by spraying, of a thin film of polymer surrounding the granule core. The coating solution contains a polymer in a suitable liquid solvent and optionally mixed together with other ingredients such as plasticizers, pigments and/or colorants. After spraying, the drying conditions permit to remove substantially all of the solvent.

The particular coating material used is not critical to the present invention, and depends upon the purpose of the coating material, e. g. the release profile, taste-masking, the ability to stay intact and/or to withstand the mechanical stress of compaction without cracking and so on. Non-limiting examples of coating polymers useful for controlling the release properties of the active agent and/or taste masking are well known in the art and include derivatives of cellulose such as methylcellulose, hydroxypropylmethylcellulose and ethylcellulose, polyvinylpyrrolidone and amino-alkylmethylacrylate copolymers. Examples of coating polymers useful for imparting resistance to gastric fluid include shellac, cellulose acetate phthalate, polyvinylacetate, hydroxypropyl methylcellulose acetate succinate, polyvinyl acetate phthalate (PVAP) styrene/acrylic acid copolymers, methacrylic acid copolymers (e.g. Eudragit™), maleic anhydride copolymers, copolymers based on ethylacrylate or methylacrylate, copolymers of acrylic or methacylic acid esters with quaternary ammonium groups, and the like. A possible coating is a film of a polymeric gastro-resistant and enterosoluble material, in order to allow activation of the pharmaceutical pellet composition only after it has reached the duodenal-intestinal tract, i.e. more preferably, in order to release the active ingredient in the duodenal-intestinal tract. Cellulose acetophtalate, cellulose acetopropionate, cellulose trimellitate, hydroxypropyl methylcellulose phthalate, hydroxypropyl methylcellulose acetate succinate, shellac, acrylic and methacrylic polymers and copolymers having different molecular weight and solubility depending on pH values may be used for this purpose. In a particular embodiment the coating is a sustained release coating.

Examples of plasticizers which may be mixed together with the coating polymer include, without limitation, polyethyleneglycol, glycerol, phtalate esters, triethylcitrate, etc. In a particular embodiment, the coat layer does not comprise partially hydrolyzed polyvinyl alcohol.

The thickness of the coating layer used is not critical to the present invention. It depends upon the desired release profile of the active agent and typically is in the micron ranges. In a particular embodiment, a coating level of at least about 10%, more specific at least 15%, and even more specific at least 20% (w/w) (percentage based on weight of the granule) is envisaged for sustained release kinetics.

Optionally and before coating, the granules can be covered with a talc layer (optionally together with polysorbate 80).

The granules as described herein, may be used in tablets, capsules, packets and other (compressed) pharmaceutical dosage forms or formulations. These formulations may further optionally contain additives typically used in the formulation of such articles, for instance flavoring agents (such as anethole, vanillin, ethyl vanillin, and the like), lubricants (such as magnesium stearate), sweeteners (such as sucrose, mannitol, aspartame, saccharin and its salts), colorants and/or buffering agents.

The oral dosage form of the present invention is particularly useful for the controlled, sustained and/or immediate release of one or more active agents. As used herein, "controlled" or "sustained" release refers to the release of an active ingredient from a pharmaceutical dosage form at a predetermined rate. "Immediate release" implies that the majority of the drug is released from the dosage form upon contact with a biological environment. For example, in case of an oral dosage form, the majority of the drug in the dosage form will burst off upon contact with the acidic environment of the stomach. In a particular embodiment of this invention, the dosage form as described herein provides an immediate release in which the majority, i.e. about 70, 75, 80, 85, 90, 95 or 100%, of the active agent(s) is released within the first hour after administration of the dosage form or composition comprising it, preferably within the first 50, 40 or 30 minutes, most preferably within the first 20 minutes. The release profile can be determined in vitro as described in the present examples, e.g. in USP hydrochloric acid (pH 1) at 37° C. in an USP Apparatus 2.

Also part of the present invention is a method to prepare the granules as provided herein. A preferred method to prepare spherical granules is by extrusion-spheronization; more in particular by cold extrusion-spheronization. This is the most employed technique as it offers the advantage to incorporate high amounts of active pharmaceutical ingredient, without producing an excessively large particle of drug-loaded granules apart from being more efficient than the other techniques for producing granules. Extrusion can be defined as the process of forcing a material through an orifice or die under controlled conditions (cold extrusion generally occurs at (near) room temperature, and max. at 50° C.) thus forming cylinders or strands called extrudates. During spheronization, these extrudates are broken into small cylinders and consequently rounded into spheres (granules; pellets). Hence, extrusion/spheronization is a multiple-step process capable of making uniformly sized spherical particles referred to as pellets and involving the following sequential steps: (1) dry mixing or blending of ingredients (powders), (2) wet mixing or granulation (i.e. wetting the mix or blend from step (1)), (3) extrusion of the wet mass into extrudates, (4) spheronization of the extrudate, (5) drying of the resulting pellets, and (6) optional coating.

In said process, the active agent(s), partially hydrolyzed PVOH and a diluent, are mixed, wetted (to the extent that is needed to allow the composition to be extruded), and granulated in a granulator such as a rapid mixer granulator, planetary mixer, fluid bed processor, centrifugal granulator and the like.

In one aspect of the invention, the active agent(s) and other compounds may be dissolved, dispersed and/or emulsified in a liquid. Demineralized water, ethanol, isopropanol, aceton, and the like, and/or an aqueous solution of partially hydrolyzed PVOH can be used as granulation liquid or solvent. The moistened mass is extruded through a perforated mesh in order to produce extrudates (cylindrical filaments). The port of the meshes determines the diameter of the extrudates and in one embodiment is from about 0.2 mm to 3 mm, in particular from about 0.5 mm to about 2 mm. The extrusion may be carried out using single screw, double screw, "sieve and basket" kind, "roll extruder", "ram extruder" extruders or any other pharmaceutically acceptable means to produce extrudates. The extrudates obtained by extrusion are then spheronized to obtain spherical particles. The spheronization device consists of a hollow cylinder with a horizontal rotating plate. The extrudates are broken in short segments which are transformed to pellets on the upper surface of a rotating plate, and in one aspect of the invention at a velocity ranging from about 200 rpm to about 2,000 rpm. The pellets may be dried in any pharmaceutically acceptable way, such as drying at room temperature and may be accomplished in any apparatus known in the art including without limitation, in an oven, a fluidized bed, or a microwave oven.

The spherical particles are dried and sieved to get the desired fraction. The dried pellets of desired particle size can optionally be further coated. Alternatively, the extruded particles are dried and sieved to get the desired fraction. Coating of particles is performed in appropriate coating equipment, e.g., centrifugal coater, coating pan, rotor process, fluid bed coater, and the like.

Other methods of granulation known in the art which involve high shear may be used to form the pellets including fluid-bed and rotogranulation, centrifugal granulator, or high-shear granulation.

The granules as described herein are preferably formulated for oral or buccal drug delivery, and in particular, are for oral delivery for release of the active agent(s) into the gastro-intestinal tract. Preferably, the granule of the present invention is shaped as or incorporated into (solid) dosage forms for oral administration such as but not limited to tablets, pills and capsules. In a specific embodiment, the dosage form is a multiparticulate form, meaning that it consists of a multiplicity of small discrete units (e.g. particles), each exhibiting some desired characteristics. In these systems, the dosage of the drug substance(s) or active ingredient(s) is divided in granules/particles which typically belong to the multi-particulate drug delivery forms. Multiparticulates are less dependent on gastric emptying rate, have a lower tendency for local irritation and have a reduced risk of dose dumping.

Additional pharmaceutical excipients known in the art may be added to the dosage form to impart satisfactory processing, disintegration, or other characteristics to the formulation. Such excipients include, but are not limited to, flow enhancers, surfactants, lubricants and glidants, disintegrants, colors, fillers such as lactose, dicalcium diphosphate, mannitol, starch and derivates, glucose and R-cyclodextrine, pigments, flavors and sweetening agents. These excipients are well known in the art and are limited only by compatibility and characteristics desired. Examples of useful liquid diluents are oils, water, alcohols, or mixtures thereof, with or without the addition of pharmaceutically suitable surfactants, suspending agents, or emulsifying agents. Lubricants and glidants include talc, magnesium stearate, calcium stearate, stearic acid, glyceryl behenate, mineral oil, polyethylene glycol, sodium stearyl fumarate, stearic acid, vegetable oil, zinc stearate, and silicon dioxide. Disintegrants suitable for the present invention include starches, algins, gums, croscarmelose, crospovidone, sodium starch glycolate, sodium lauryl sulfate, microcrystalline cellulose, polacrilin potassium, and methylcellulose. In a particular embodiment, the dosage form of the invention comprises a filler.

The terms "drug", "active agent", "active ingredient" or "pharmaceutically active ingredient" will be used interchangeably herein. The (core of the) oral dosage form of the invention typically contains one, two, three or more active agents.

The active agent(s) that may be administered using the formulations, systems and methods of the invention are not limited, as the invention enables the effective delivery of a wide variety of active agents. The term "active agent/ingredient or drug" as used herein refers to therapeutic, diagnostic, cosmetic or prophylactic pharmaceutical and veterinary agents as well as other agents. The active ingredient(s) is present in at least the core of the granule. The particular nature of the active ingredient is not critical, and pharmaceutical and non-pharmaceutical active ingredients, such as nutritional supplements, detergents, dyes, pesticides, agricultural chemicals, enzymes, and foods may also be employed.

The therapeutic or active agent may be selected from any of the various classes of such agents including, but not limited to, analgesic agents such as acetaminophen, ibuprofen and tramadol, anesthetic agents, anti-anginal agents, antiarthritic agents, anti-arrhythmic agents, antiasthmatic agents, antibacterial agents, anti-BPH agents, anticancer agents, anticholinergic agents, anticoagulants, anticonvulsants, antidepressants, antidiabetic agents such as metformin, antidiarrheals, anti-epileptic agents, antifungal agents, antigout agents, antihelminthic agents, antihistamines, antihypertensive agents, anti-inflammatory agents such as ibuprofen, antimalarial agents, antimigraine agents such as acetaminophen and ibuprofen, antimuscarinic agents, antinauseants, antineoplastic agents, anti-obesity agents, antiosteoporosis agents, antiparkinsonism agents, antiprotozoal agents, antipruritics, antipsychotic agents, antipyretics such as acetaminophen and ibuprofen, antispasmodics, antithyroid agents, antitubercular agents, antiulcer agents, anti-urinary incontinence agents, antiviral agents, anxiolytics, appetite suppressants, attention deficit disorder (ADD) and attention deficit hyperactivity disorder (ADHD) drugs, calcium channel blockers, cardiac inotropic agents, beta-blockers, central nervous system stimulants, cognition enhancers, corticosteroids, COX-2 inhibitors, decongestants, diuretics e.g. Hydrochlorothiazide (HCT), gastrointestinal agents, genetic materials, histamine receptor antagonists, hormonolytics, hypnotics, hypoglycemic agents, immunosuppressants, keratolytics, leukotriene inhibitors, lipid-regulating agents, macrolides, mitotic inhibitors, muscle relaxants, narcotic antagonists, neuroleptic agents, nicotine, nutritional oils, parasympatholytic agents, sedatives, sex hormones, sympathomimetic agents, tranquilizers, vasodilators, vitamins, and combinations thereof.

Active agents according to the invention also include nutrients, cosmeceuticals, diagnostic agents, and nutritional agents. Some agents, as will be appreciated by those of ordinary skill in the art, are encompassed by two or more of the aforementioned groups.

Anti-microbial agents such as broad spectrum antibiotics for combating clinical and sub-clinical infection, for example gentamycin, vancomycine and the like are also appropriate. Other suitable therapeutic agents are naturally occurring or synthetic organic or inorganic compounds well known in the art, including non-steroidal anti-inflammatory drugs, proteins and peptides (that may be produced either by isolation from natural sources or through recombination), hormones (for example androgenic, estrogenic and progestational hormones such as oestradiol), bone repair promoters, carbohydrates, antineoplastic agents, antiangiogenic agents, vasoactive agents, anticoagulants, immunomodulators, cytotoxic agents, antiviral agents, antibodies, neurotransmitters, oligonucleotides, lipids, plasmids, DNA and the like.

Suitable therapeutically active proteins include e.g. fibroblast growth factors, epidermal growth factors, platelet-derived growth factors, macrophage-derived growth factors such as granulocyte macrophage colony stimulating factors, ciliary neurotrophic factors, tissue plasminogen activator, B cell stimulating factors, cartilage induction factor, differentiating factors, growth hormone releasing factors, human growth hormone, hepatocyte growth factors, immunoglobulins, insulin-like growth factors, interleukins, cytokines, interferons, tumor necrosis factors, nerve growth factors, endothelial growth factors, osteogenic factor extract, T cell growth factors, tumor growth inhibitors, enzymes and the like, as well as fragments thereof.

As evident for a person skilled in the art, the load of the active agent(s) comprised in the pharmaceutical dosage form according to this invention, may vary depending on the active agent(s) used, and the envisaged application area. In general, the granule, in particular the core thereof, of the invention may comprise about and between 40-95 wt. % of active agent. In a specific embodiment the granule may comprise about and between 50-90 wt. % of active agent, or about and between 50-80 wt. % of active agent, and may comprise preferably at least or about 40%, more preferably at least 45 wt. %, 50 wt. %, 55 wt. %, 60 wt. %, 65 wt. %, 70 wt. %, 80 wt. % or more wt. % of the active agent, including all values in between. As mentioned herein, any is weight-by-weight, relative to the total weight of the granule core, or optionally the formulation. As is evidenced by the present examples, the dosage form of the present invention is surprisingly useful for high drug loading, i.e. a drug loading of more than 50 wt. % can be obtained without any disadvantages. In a particular embodiment, the invention encompasses a granule comprising at least 50 wt. % of an active agent in the core, and even more particular at least 60 wt. %, 70 wt. %, 80 wt. % or even 90 wt. % of an active agent or combination of two or more active agents.

The drug release rate is tested during drug dissolution tests as e.g. described in the present examples.

The granules according to this invention may be in any suitable administration form. For example, a multiplicity of the granules may be compressed during a tableting process providing a tablet or any other compressed dosage form. Alternatively, the granules may be encapsulated. A further example is a sachet, a unit dose comprising a multiplicity of the granules as provided herein. Preferably the composition comprising the granules of the present invention is an oral dosage form.

In a further embodiment, the present invention encompasses a pharmaceutical composition comprising a dosage form as described herein and a pharmaceutically acceptable carrier, excipient and/or diluent, known to the skilled person.

In a further aspect, the present invention provides a dosage form or composition as defined herein for use as a medicament, in particular for the controlled, sustained and/or immediate release of one or more active agents.

Furthermore, the present invention provides a method for the immediate or controlled release of one or more active agents; said method comprising administering to a patient in need thereof a solid pharmaceutical dosage form as defined herein.

The present invention also provides a method of preparing a dosage form, in particular a granule; said method comprising the steps of:
mixing an active agent, partially hydrolyzed polyvinyl alcohol and a diluent, in particular MCC,
adding a liquid such as e.g. water;
extruding the wetted mixture to obtain an extrudate,
spheronizing of the extrudate to obtain a plurality of granules, and
drying the plurality of granules.

In case a partially hydrolyzed PVOH solution (e.g. dissolved PVOH in demineralized water) is used in the process, no additional wet massing liquid is needed.

In a further embodiment the method comprises the addition of a coat layer.

In addition, the present invention provides a granule obtainable by a process as defined herein.

This invention will be better understood by reference to the Examples that follow, but those skilled in the art will readily appreciate that these are only illustrative of the invention as described more fully in the claims that follow thereafter. Particular embodiments and examples are not in any way intended to limit the scope of the invention as claimed. Additionally, throughout this application, various publications are cited. The disclosure of these publications is hereby incorporated by reference into this application to describe more fully the state of the art to which this invention pertains.

EXAMPLES

In the first part of this study, PVOH was evaluated as pelletisation aid in high drug-loaded pellets produced by extrusion/spheronisation, whereby pellet properties (i.e. aspect ratio, sphericity, particle size distribution . . . ) were compared with MCC pellets as a reference. In the second part of this study, the use of those pellets in fixed dose combination therapy was investigated with an acetaminophen/tramadol.HCl formulation by which pellet quality and drug release was evaluated. Furthermore, the use of a coat and a taste masking agent was evaluated, as well as the in vivo release characteristics of the pellets.

1 MATERIALS AND METHODS 1.1 Materials

A pharmaceutical grade PVOH 4-88 (88% hydrolysed), obtained from Merck (Darmstadt, Germany), and microcrystalline cellulose (Avicel® PH101) (FMC Wallingstown, Little Island, Cork, Ireland) were used as pelletisation aids. Micronized acetaminophen (Atabay, Istanbul, Turkey), tramadol.HCl (Proto Chemicals AG, Mitlodi, Switzerland), and metformin.HCL (Granules, Jeedimetla, India) were used as model drugs. Demineralised water or an aqueous solution of PVOH were used as granulation liquid.

For coating trials, a methacrylic acid copolymer (Eudragit™ NM 30D) and hydroxypropylmethylcellulose (Methocel™ E5) were supplied by Evonik (Darmstadt, Germany) and The Dow Chemical Company (Midland, Mich., USA), respectively. Talc and polysorbate 80 (Tween 80™) were obtained from Fagron (Waregem, Belgium).

A more detailed description of the particle size and geometry of the used raw materials is listed in Table 1.

| Powder characteristics of raw materials | | | | | |
|---|---|---|---|---|---|
| | D10 ($\mu$m) | D50 ($\mu$m) | D90* ($\mu$m) | Aspect ratio | Sphericity |
| Acetaminophen | 1.7 | 6.4 | 20.1 | 0.58 | 0.84 |
| Metformin•HCl | 8.4 | 51.6 | 150.2 | 0.66 | 0.87 |
| MCC | 19.8 | 54.1 | 113.1 | 0.53 | 0.76 |

*D90 means that 90% of the particles have a size of less than the specified diameter.

1.2 Plasticity Measurements: Atterberg Limits

An ASTM standard test (ASTM D 4318) was used to quantify the liquid limit, plastic limit and plasticity index of the wet mass. The plasticity index was defined as the range of water content over which a wet mass behaves plastically. Mathematically, it was calculated as the difference between the liquid limit and the plastic limit. The liquid limit was determined by spreading an amount of the wet mass in a brass cup. A grooving tool was then used to divide the material into two symmetrical halves separated by 13 mm.

By repeatedly dropping the cup in a mechanical device, both halves were able to flow towards the centre of the cup and make contact at the bottom of the groove. As the multipoint liquid limit (i.e. method A of ASTM D 4318) was used, four trials over a wide range of water contents were performed. The number of drops required before both halves made contact with each other was plotted as a function of water content on a semi-logarithmic graph, with the water content as ordinates on the arithmetical scale, and the number of drops as abscissas on a logarithmic scale. Subsequently, the best fit line was plotted. The water content corresponding to the intersection of the line with the 25-drop abscissa was taken as the liquid limit of the wet mass. To determine the water content from each trial, a standard ASTM test (ASTM D 2216) was used. Therefore, initial masses (container plus wet mass) were recorded immediately and after 24 h oven drying at 105° C. The plastic limit was determined by alternately pressing and rolling a small amount (±12 g) of wet masses with different water content into a 3.2 mm diameter thread. The water content at which the thread crumbled and could no longer be pressed together and re-rolled was reported as the plastic limit. All experiments were performed in triplicate.

1.3 Production of Pellets

The active pharmaceutical ingredient (API), PVOH and Avicel® PH101 or API and Avicel® PH101 (batch size: 200 g) in different ratios were mixed during 5 min. in a planetary mixer (Kenwood Chief, Hampshire, UK), using a K-shaped mixing arm (Table 2). Demineralized water or a PVOH aqueous solution (prepared by dissolving PVOH in demineralized water at 80° C. and cooled down to room temperature prior to addition) was gradually added to the powder mixture, while mixing was continued during 10 min. The wet mass was extruded at an extrusion speed of 100 rpm using a single screw extruder (Dome extruder DG-L1, Fuji Paudal, Tokyo, Japan) equipped with a dome shaped extrusion screen with 1.0 mm perforations. The resulting extrudates were spheronised for 1 min. at a speed of 1000 rpm using a spheroniser having a cross-hatched geometry friction plate (Caleva Model 15, Caleva, Sturminster Newton, Dorset, UK). The pellets were oven dried for 24 h at 40° C. Each batch of pellets was sieved for 5 min. at 2 mm amplitude using a sieve shaker (Retsch, Haan, Germany) to obtain the 0.710-1.00 mm size fraction.

TABLE 2

Composition of pellet formulations

| Formulation | Acetaminophen | PVOH | MCC | Ratio (PVOH/MCC) | Water content (%)* |
|---|---|---|---|---|---|
| 1 | 70 | 0 | 30 | 0/100 | — |
| 2 | 70 | 1.5 | 28.5 | 5/95 | 53.3 |
| 3 | 70 | 3 | 27 | 10/90 | 46.2 |
| 4 | 70 | 6 | 24 | 20/80 | 38.3 |
| 5 | 70 | 15 | 15 | 50/50 | — |
| 6 | 80 | 0 | 20 | 0/100 | — |
| 7 | 80 | 1 | 19 | 5/95 | 43.3 |
| 8 | 80 | 2 | 18 | 10/90 | 40.6 |
| 9 | 80 | 4 | 16 | 20/80 | 33.2 |
| 10 | 80 | 10 | 10 | 50/50 | 22.9 |
| 11 | 90 | 0 | 10 | 0/100 | — |
| 12 | 90 | 0.5 | 9.5 | 5/95 | 36.3 |
| 13 | 90 | 1 | 9 | 10/90 | 35.0 |
| 14 | 90 | 2 | 8 | 20/80 | 30.2 |
| 15 | 90 | 5 | 5 | 50/50 | 24.5 |
| 16 | — | — | 100 | — | 120 |
| 17 | 50 | — | 50 | — | 55.7 |

| Form. | Metformin•HCl | PVOH | MCC | Ratio (PVOH/MCC) | Water content (%)* |
|---|---|---|---|---|---|
| F18 | 90 | 0 | 10 | 0/100 | — |
| F19 | 88.7 | 1.5 | 9.8 | 13/87 | 18.5 |
| F20 | 87.3 | 2.9 | 9.7 | 23/77 | 17.0 |

*Water content was calculated as a percentage of the total dry weight of each formulation 1.4 Evaluation of Different PVOH Grades Acetaminophen and Avicel® PH101 (with or without the addition of different PVOH grades, Table 3) were dry mixed in different ratios during 5 min in a planetary mixer (Kenwood Chief, Hampshire, UK), using a K-shaped mixing arm. The aqueous PVA solution was gradually added to the powder mixture. After 10 min of mixing, the wet mass was extruded at an extrusion speed of 100 rpm using a single screw extruder (Dome extruder DG-L1, Fuji Paudal, Tokyo, Japan) equipped with a dome-shaped extrusion screen having a thickness of 1.2 mm and 33 1 mm-perforations per cm². The resulting extrudates were spheronized for 1 min at a speed of 1000 rpm using a spheroniser having a cross-hatched geometry friction plate (Caleva Model 15, Caleva, Sturminster Newton, Dorset, UK) with a diameter of 38 cm. The features on the friction plate had a size of 6.5 mm and were positioned at a distance of 3.5 mm of each other.

TABLE 3

Composition of the pellet formulations. For each formulation F1-F5 resp., all experiments were conducted using different PVOH grades (i.e. PVA505, 4-88, 5-88, 8-88, 16-88, 26-88 and 40-88).

| Form. | Concentration (%) | | | Ratio | Water content |
|---|---|---|---|---|---|
| | Acetaminophen | PVOH | MCC | (PVOH/MCC) | (%)* |
| F1 | 90 | 0 | 10 | 0/100 | — |
| F2 | 90 | 0.5 | 9.5 | 5/95 | 36.3 |
| F3 | 90 | 1 | 9 | 10/90 | 35.0 |
| F4 | 90 | 2 | 8 | 20/80 | 30.2 |
| F5 | 90 | 5 | 5 | 50/50 | 24.5 |

*Water content was calculated as a percentage of the total dry weight of each formulation

1.5 Preparation of Sustained Release Pellets by Coating

The coating suspension (batch size 1 kg) was prepared in four steps: (1) 10 g of HPMC was added to 559.7 g demineralized water. Subsequently, the mixture was heated to 55° C. and mixed using a high speed mixer (Silverson™ L4R, Silverson Machines, Waterside, Chesham, Bucks, England) until a clear solution was obtained; (2) 30.3 g of a 33% aqueous solution of polysorbate 80 and 100 g talc were added and dispersed for at least 10 min; (3) the resulting excipient suspension was slowly poured into 300 g Eudragit™ NM 30D with a magnetic stirrer at room temperature for 5 min; (4) the spray suspension was passed through a 0.5 mm sieve and was then continuously stirred with a magnetic stirrer at room temperature during coating experiments.

Varying coating levels (0, 8, 14 and 20%, w/w) were applied to pellets containing 87.3% (w/w) metformin.HCl (F20 in Table 2, sieve fraction 850-1120 μm). All experiments were performed using a laboratory scale fluid bed granulator (GPCG 1, Glatt, Binzen, Germany). The spray suspension was added at a flow rate of 1.85 mL/min through a 0.8 mm nozzle (bottom spray). The atomizing pressure and inlet air temperature were set at 2 bar and 40° C., respectively. The resulting outlet air temperature and product temperature were between 20 and 25° C. An inlet air velocity of 5 m/s was used and the filter bags were shaken every 15 s for a period of 5 s. All coated pellets were cured in an oven at 40° C. for 24 h. An overview of their final composition is listed in Table 4.

TABLE 4

Composition of coated metformin•HCl pellet formulations.

| Form. | Concentration (%) | | | |
|---|---|---|---|---|
| | Metformin•HCl | PVOH | MCC | Coating |
| F21 | 87.3 | 2.9 | 9.7 | 0.0 |
| F22 | 80.4 | 2.7 | 8.9 | 7.9 |
| F23 | 74.9 | 2.5 | 8.3 | 14.2 |
| F24 | 69.5 | 2.3 | 7.7 | 20.4 |

1.6 Taste Masking

Usually, the drug load of taste masked pellets is limited as large amounts of MCC (to enable extrusion-spheronisation) and taste masking polymer are needed. As the MCC concentration could be lowered by the addition of PVA, it was the aim to develop high drug loaded taste masked ibuprofen pellets.

Ibuprofen and Avicel® PH101 (with or without the addition of different PVA concentrations, Table 5a) were dry mixed in different ratios during 5 min in a planetary mixer (Kenwood Chief, Hampshire, UK), using a K-shaped mixing arm. The aqueous PVA solution was gradually added to the powder mixture. After 10 min of mixing, the wet mass was extruded at an extrusion speed of 100 rpm using a single screw extruder (Dome extruder DG-L1, Fuji Paudal, Tokyo, Japan) equipped with a dome-shaped extrusion screen having a thickness of 1.2 mm and 33 1 mm-perforations per cm2. The resulting extrudates were spheronized for 1 min at a speed of 1000 rpm using a spheroniser having a cross-hatched geometry friction plate (Caleva Model 15, Caleva, Sturminster Newton, Dorset, UK) with a diameter of 38 cm. The features on the friction plate had a size of 6.5 mm and were positioned at a distance of 3.5 mm of each other.

TABLE 5a

Composition of the pellet formulations. All experiments were conducted using PVA4-88.

| Form. | Concentration (%) | | | Ratio | Water content |
|---|---|---|---|---|---|
| | Ibuprofen | PVA | MCC | (PVA/MCC) | (%)* |
| F1 | 80 | 0 | 20 | 0/100 | — |
| F2 | 80 | 1 | 19 | 5/95 | 43.3 |
| F3 | 80 | 2 | 18 | 10/90 | 40.6 |
| F4 | 80 | 4 | 16 | 20/80 | 33.2 |

*Water content was calculated as a percentage of the total dry weight of each formulation Formulations with different PVA content were processed. The PVA/MCC ratios tested at a constant drug load of 80% (w/w). Whereas high drug-loaded formulations without the addition of PVA (i.e. F1 in Table 5a) could not be processed via extrusion-spheronisation due to shark skinning and the high brittleness of the extrudates during spheronisation, the addition of a low PVA concentration improved the extrusion properties of the formulations, yielding extrudates with a smooth surface, even for formulations with a low MCC content (e.g. F3 containing 80% ibuprofen, 2% PVOH and only 18% MCC).

Based on its high drug content and low friability (0.54±0.12%), formulation 3 (F3) was selected as starting material for coating trials.

TABLE 5b

Composition of coated ibuprofen pellet formulations.

| Form. | Concentration (%) | | | |
|---|---|---|---|---|
| | Ibuprofen | PVA | MCC | Coating |
| F5 | 67.6 | 2.3 | 16.9 | 13.2 |

1.7 Characterization
1.7.1 Pellet Size and Shape

The size and shape of the pellets were determined using dynamic image analysis (QicPic, Clausthal-Zellerfeld, Germany). $D_{10}$, $D_{50}$ and $D_{90}$, which are the respective particle sizes at 10, 50 and 90% cumulative undersize, were determined (Kooiman et al., 2009). Furthermore, the width of the particle size distributions (PSD) was determined by calculating the span, as follows:

$$\text{Span (µm)} = D_{90} - D_{10}$$

An independent sample t-test was performed with SPSS Statistics 23 (IBM, New York, United States) to detect significant differences in span between formulations. The shape of the pellets was expressed as aspect ratio (AR) and sphericity. AR was defined as the ratio of the maximal and minimal Feret diameter ($\text{Feret}_{max}$ and $\text{Feret}_{min}$, respectively).

$$AR = \frac{\text{Feret}_{max}}{\text{Feret}_{min}}$$

Sphericity was defined as the ratio between the perimeter of a circle that has the same projected area (A) as the particle ($P_{EQPC}$) to the measured perimeter ($P_{REAL}$), and is thus a value between 0 and 1 (Yu and Hancock, 2008).

$$\text{Sphericity} = \frac{P_{EQPC}}{P_{REAL}} = \frac{2\sqrt{\pi A}}{P_{REAL}}$$

The measurements were performed in triplicate (±10 g for each sample).

1.7.2 Loss on Drying (LOD)

After drying, the residual moisture content of the pellets was analysed by loss on drying (LOD) using a Mettler LP16 moisture analyser, including an infrared dryer and a Mettler PM460 balance (Mettler-Toledo, Zaventem, Belgium). A sample of approximately 2 g was dried at 105° C. until the rate of change was less than 0.1% LOD for 30 s and the % LOD was then recorded. The measurements were performed in triplicate.

1.7.3 Friability

Pellet friability was determined using a friabilator equipped with an abrasion drum (Pharma Test, Hainburg, Germany). Approximately 10 g of pellets within the size range of 0.710 to 1.00 mm were accurately weighed and added to the abrasion drum together with 200 glass beads (4 mm in diameter). The friabilator was set at 25 rpm during 10 min. At the end of the run, the content of the abrasion drum was sieved onto a sieve of 0.5 mm or 850 µm and the fraction below 0.5 mm or 850 µm was accurately weighed. Friability was measured in triplicate and calculated as follows:

$$\text{Friability}(\%) = \frac{\text{Fraction} < 0.5 \text{ mm (g)}}{\text{Total sample (g)}} \times 100$$

or $$\text{Friability \%} = \text{Fraction} < 850 \text{ µm (g)} \quad \text{Friability}(\%) = \frac{\text{Fraction} < 850 \text{ µm (g)}}{\text{Total sample (g)}} \times 100$$

1.7.4 Image Analysis

Photomicrographs of pellets were taken with a digital camera (Camedia® C-3030 Zoom, Olympus, Tokyo, Japan), linked with a stereomicroscope system (SZX9 DF PL 1.5×, Olympus, Tokyo, Japan). A cold light source (Highlight 2100, Olympus, Germany) and a ring light guide (LG-R66, Olympus, Germany) were used to obtain top light illumination of the pellets against a dark surface.

Scanning electron microscopy (SEM) was used to determine differences in pellet surface morphology. Prior to imaging, samples were coated with a thin gold layer. SEM images were recorded using a tabletop SEM (PHENOM™, FEI Company).

1.8 In Vitro Dissolution

Drug release from pellets was determined using USP apparatus 2 (paddles), in a VK 7010 dissolution system combined with VK 8000 automatic sampling station (Vankel Industries, New Jersey, USA). The amount of pellets corresponding to 500 mg acetaminophen or 325 mg acetaminophen and 37.5 mg tramadol.HCl were placed in 0.1 N HCl pH 1 (900 ml, at a temperature of 37±0.5° C.), while the rotational speed of the paddles was 100 rpm. Samples of 5 ml were withdrawn at 10, 20, 30, 40, 50, 60, 70, 80, 100 and 120 min. (without medium replacement) and spectrophotometrically analyzed for acetaminophen concentration at 244 nm by means of a Shimadzu UV-1650PC UV-VIS double beam spectrophotometer (Antwerpen, Belgium). The acetaminophen content in the samples was determined by linear regression using a calibration curve between 1.5 and 15 µg/ml. Tramadol.HCl was analyzed via 'high performance liquid chromatography' (HPLC). The HPLC system (Merck-Hitachi D-7000, Tokyo, Japan) consisted of a pump (Merck-Hitachi L-7200), an autosampler (Merck-Hitachi L-7250), a LichroSpher 100 RP-8 column (4.6×150 mm, 5 µm) (Merck Millipore, Darmstadt, Germany), and an UV-detector (Merck-Hitachi L-7400) set at 272 nm. For the preparation of the mobile phase, 0.05 M monobasic potassium phosphate was mixed with acetonitrile (Biosolve, Valkenswaard, the Netherlands) in a ratio 4:1 (vol/vol). The analyses were performed at 25° C., and the flow rate was set at 1 ml/min. A volume of 25 µL was injected onto the HPLC system. Each formulation was evaluated in triplicate.

Drug release from (un)coated metformin hydrochloride pellets was determined using the paddle method on a VK 7010 dissolution system (VanKel Industries, New Jersey, USA) at a speed of 100 rpm. An amount of pellets corresponding to 250 mg metformin.HCl was placed in 900 mL 0.1 N HCl (pH 1.2) or phosphate buffer solution (pH 6.8), set at a temperature of 37±0.5° C. Samples were withdrawn at 0.5, 1, 2, 4, 6, 8, 12, 16, 20 and 24 h, and spectrophotometrically (UV-1650PC, Shimadzu Benelux, Antwerp, Belgium) analysed using a wavelength of 232 nm.

1.9 In Vivo

The bioavailability study (application ECD 2013/127) was approved by the Ethical Committee of the Faculty of Veterinary Medicine (Ghent University).

1.9.1 Animal Study

In vivo experiments were performed using a sustained release pellet formulation described above (i.e. F24) and a reference formulation (Glucophage™ SR 500 mg, ½ tablet). Open label cross-over assays were performed on 6 male beagle dogs (10-13 kg) with a wash-out period of at least 8 days. The pellet and reference formulations were orally administered to fasted dogs (no food intake was allowed 12 h prior to drug administration) with 20 mL water. During the experiment the dogs were only allowed to drink water. Blood samples were collected after 1, 2, 3, 4, 5, 6, 8 and 12 h post administration, and were stored at −25° C. until analysis.

1.9.2 Metformin Assay

An extraction method developed by Gabr et al., 2010, was optimized. After de-freezing, plasma samples were centrifuged using a Centric 322A (Tehtnica, Slovenia) at 2300 g for 10 min. 280 µL of the supernatant was spiked with 20 µL 0.05 mg/mL ranitidine solution. During a first extraction step, 50 µL 10 M sodium hydroxide solution and 3 mL organic phase (1-butanol/hexane, 50/50, v/v) were added. The tubes were mixed using a Turbula™ mixer (Willy A. Bachofen Maschinenfabrik, Switzerland) for 30 min at an intensity of 79 rpm. After centrifugation the upper organic layer was transferred to a clean test tube. Back extraction was performed by adding 1 mL 2M HCl, mixing the tubes (79 rpm, 10 min) and centrifugation (10 min, 2300 g). Afterwards the organic layer was removed, and 400 µL sodium hydroxide (10 M) and 2 mL organic phase (1-butanol/hexane, 50/50, v/v) were added. After mixing (79 rpm, 30 min) and centrifugation (10 min, 2300 g) the organic layer was transferred into a clean glass tube and evaporated to dryness under a nitrogen stream.

The HPLC system (Merck-Hitachi, Darmstadt, Germany) consisted of an isocratic solvent pump (L-7100) set at a constant flow rate of 0.7 mL/min, an auto-sampler injection system (L-7200) with a 100 µL loop (Valco Instruments Corporation, Houston, Tex., USA), a reversed-phase column and pre-column (LiChroCart® 250-4 and LiChrospher® 100RP-18 5 µm, respectively) and a variable wavelength UV-detector (L-7400) set at 236 nm. The mobile phase composition remained constant over time and consisted of potassium dihydrogen phosphate buffer (adjusted to pH 6.5 with 2 M NaOH)/acetonitrile (66/34, v/v) and 3 mM sodium dodecyl sulphate (SDS).

1.9.3 Data Analysis

Peak integration was performed using the software package D-7000 HSM Chromatography Data Manager. The peak plasma concentration ($C_{max}$), time to reach $C_{max}$ ($T_{max}$), half value duration ($HVD_{t50\% \, Cmax}$) and area under the curve ($AUC_{0-12 \, h}$) were calculated using a commercial software package (MATLAB 8.6, The MathWorks, Natick, USA, 2015). The sustained-release characteristics of the formulation were evaluated by calculating the $R_D$ ratio between the $HVD_{t50\% \, Cmax}$ values of a test formulation and an immediate-release formulation. A ratio of 1.5, 2 and >3 indicates low, intermediate and strong sustained release characteristics, respectively. A $HVD_{T50\% \, Cmax}$ value of 3.2 h for immediate release metformin tablets, administrated to beagle dogs, was abstracted from literature and used to calculate the $R_D$ ratio. (Meier et al. 1974; Gabrielsson et al. 2000; Lalloo et al. 2012).

1.9.4 Statistical Analysis

The effect of metformin.HCl formulation on the bioavailability was assessed using an independent sample t-test. The normality of the residuals was evaluated with a Kolmogorov-Smirnov test. To test the assumption of variance homogeneity, a Levene's test was used. The statistical analysis was performed using SPSS (IBM SPSS Statistics for Windows, version 23.0, Armonk, N.Y., USA, 2015).

2 RESULTS AND DISCUSSION

2.1 Evaluation of PVOH as Pelletisation Aid for the Production of Acetaminophen Pellets Pellets with acceptable quality containing only acetaminophen and MCC could be processed with a maximum drug concentration of 50% and a water content of 55.6% (F17). O'Connor et al. similarly observed that MCC (Avicel PH-101) did not yield acceptable pellets at higher drug concentration (Oconnor and Schwartz, 1985). In this study PVOH was evaluated as pelletisation aid, in order to raise drug concentration inside the pellets. However, preliminary studies have shown that a minimal MCC concentration (5%) was required to overcome problems related to the tackiness effect of PVOH during extrusion, and to improve water tolerance of the formulation (Mallipeddi et al., 2010). MCC acts like a 'molecular sponge', which is able to absorb and retain large quantities of water due to its large surface area and high internal porosity, and therefore hold water when pressure was applied during extrusion (Fielden et al., 1988).

Fifteen formulations were processed, whereby acetaminophen concentration ranged from 70% to 90% and the ratio PVOH/MCC ranged from 0/100 to 50/50 (Table 2). The formulations without PVOH could not be spheronised, as the extrudates were to brittle and broke up inside the spheroniser (F1, F6 and F11). Formulation 5, containing 15% PVOH and acetaminophen as active ingredient, was not processable as the extrudates sticked together after exiting the extruder.

Lower water content was required for formulations containing higher acetaminophen concentration and PVOH/MCC ratio, mainly due to a decreased MCC concentration, because MCC has a large water-holding capacity (Chatlapalli and Rohera, 1998) (Verheyen et al., 2009). Additionally, Law et al. studied the use of hydrophilic polymers with MCC to improve extrusion/spheronisation, and indicated that more adhesive polymers required lower levels of water, as over-hydration caused agglomeration (Law and Deasy, 1998). Therefore, formulations containing an increased PVOH concentration, required a reduced water content.

Pellets were prepared with PVOH added as a dry powder or predissolved in water. Three formulations were processed via the dry addition method (i.e. F10, F12 and F13). After drying, the residual moisture content was below 1.5% for all formulations.

The particle size distributions (PSD) of different formulations were compared with reference pellets made of pure MCC pellets (F16) (FIG. 1).

The pellet size of formulations containing PVOH was higher compared to the reference. J. Chatchawalsaisin et al. reported that pellet dimensions depended on extrudate diameter and length to which the extrudate was chopped (Chatchawalsaisin et al., 2005). During extrusion, it was noticed that extrudates containing PVOH were longer compared to MCC extrudates. Therefore, PVOH extrudates broke into longer segments during spheronisation and provide bigger pellets accordingly. Additionally, pellet size could also increase due to mass transfer between pellet particles. M. Koester et al. reported that besides plastic deformation, mass transfer must be considered during spheronisation (Koester and Thommes, 2010). Microscopic images showed agglomeration of smaller particles on the surface of the pellets (data not shown), which could consolidate with the larger pellets during spheronisation (plastic deformation), leading to a higher particle size.

Pellets developed for pharmaceutical applications, are required to have a narrow PSD (Dukic-Ott et al., 2009). Therefore, the span, which indicates the width of the PSD was determined and reported in Table 6. A small span corresponds with a narrow PSD.

TABLE 6

Span ($d_{90}$-$d_{10}$, μm) (mean ± standard deviation, n = 3) of formulations as a function of drug concentration (70-90%), PVOH/MCC ratio (0/100 – 50/50). PVOH was added either as dry powder or aqueous dispersion. The significance of the results was determined with independent sample t-test. Span values in the same row with different superscripts are different at the 0.05 level of significance.

|  | Formulation | PVOH method addition | |
|---|---|---|---|
|  |  | Dry | Wet |
| 70% | F2 | 1486 ± 348[a] | 640 ± 23[b] |
|  | F3 | 1040 ± 85[a] | 679 ± 52[b] |
|  | F4 | 1158 ± 197[a] | 467 ± 32[b] |
| 80% | F7 | 1198 ± 181[a] | 1114 ± 64[a] |
|  | F8 | 926 ± 42[a] | 998 ± 35[a] |
|  | F9 | 965 ± 68[a] | 803 ± 22[b] |
| 90% | F14 | 1143 ± 198[a] | 1172 ± 355[a] |
|  | F15 | 2338 ± 253[a] | 805 ± 73b |
| Ref. | MCC |  | 434 ± 19 |

An independent sample t-test was used to detect significant differences in span between formulations either processed with PVOH in dry powder form or solution. In general, the use of PVOH solution caused a significant (P<0.05) decrease in span, possibly due to the fact that PVOH solution, which act as a liquid binder, was more homogenously distributed during granulation. R. Chatlapalli also reported that the use of a liquid binder (i.e. hydroxypropyl cellulose in isopropyl alcohol) was more effective than in dry powder form (Chatlapalli and Rohera, 1998). If PVOH/MCC ratio was raised, a narrower PSD was obtained. F4 combined with the wet addition method for PVOH resulted in the lowest span (467±32 μm) and did not show significant difference (p>0.05) with the reference MCC pellets. However, it was noticed that increasing the drug load from 70% to 90% and thereby decreasing the amount of PVOH and MCC in the pellets, had a negative influence on the span. This indicates that PVOH and MCC were required to provide sufficient rigidity, plasticity and water absorbing capacity to allow production of spheres with narrow PSD (Wlosnewski et al., 2010). Overall, the span values of formulations containing PVOH were higher, and thus PSD broader.

Using a standard test for measuring the plasticity index of soil (i.e. the Atterberg method, ASTM D 4318) the impact of PVOH addition on the plasticity of the wet mass was determined. Whereas an increase of drug content in MCC formulations was correlated with a drop of the plasticity index (20.7 for a 50/50 API/MCC mixture vs. 4.8 and 8.9 for formulations containing 80% paracetamol and 90% metformin, respectively), the addition of PVOH significantly improved the plasticity of the wet mass which is an important factor during an extrusion-spheronisation process (Table 7).

TABLE 7

Plasticity indexes (mean ± SD, n = 3) of the wet mass used for the manufacturing of different pellet formulations.

| | Concentration (%) | | | |
|---|---|---|---|---|
| Form. | Acetaminophen | PVOH | MCC | Plasticity index (%) |
| F6 | 80 | 0 | 20 | 4.8 ± 1.3 |
| F7 | 80 | 1 | 19 | 4.9 ± 0.4 |
| F8 | 80 | 2 | 18 | 12.3 ± 3.0 |
| F9 | 80 | 4 | 16 | 16.5 ± 0.1 |
| F10 | 80 | 10 | 10 | 48.5 ± 1.3 |
| F17 | 50 | — | 50 | 20.7 ± 3.0 |

| Form. | Metformin•HCl | PVOH | MCC | Plasticity index (%) |
|---|---|---|---|---|
| F18 | 90 | 0 | 10 | 8.9 ± 1.8 |
| F20 | 87.3 | 3 | 9.7 | 17.9 ± 0.9 |

A plasticity index of the wet mass about and between 5% and 30%, in particular between 10% and 20%, and more in particular between 12% and 20% resulted in enhanced extrusion spheronization properties, even at high drug load.

Figure 2:
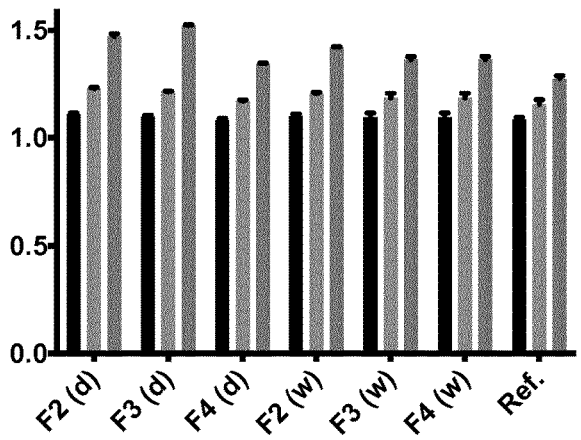
FIG. 2: Aspect ratio and sphericity (mean±SD, n=3) of formulations as a function of particle size (■ D10, ▨ D50 and ▨ D90), PVA/MCC ratio (5/95-20/80%) and drug load (70-90%). PVA was added either dry (d) or wet (w). MCC pellets without drug were used as reference (Ref.). Sieve fraction 710-1000 μm was used (n=3).
Figure 2:
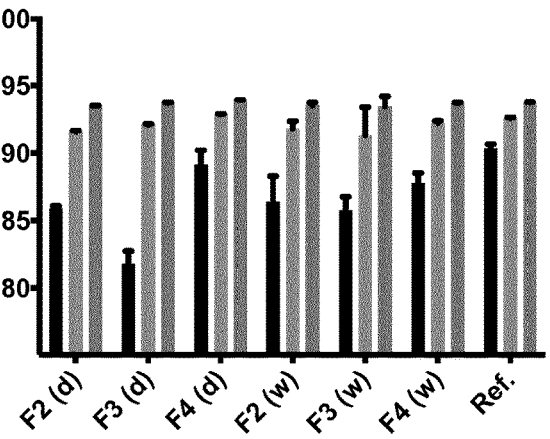
Figure 2:
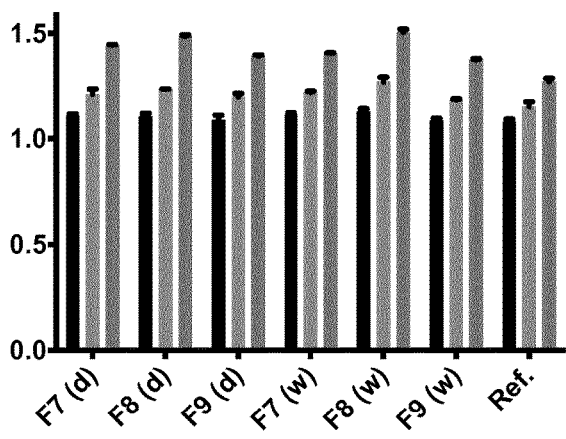
Figure 2:
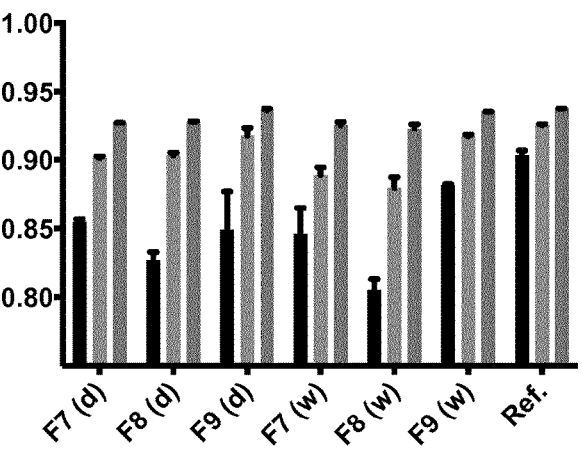
Figure 2:
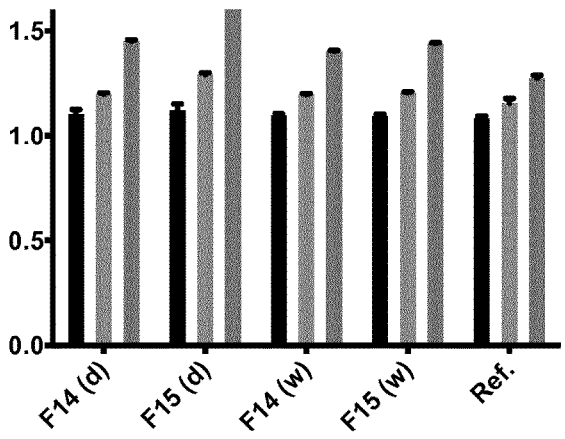
Figure 2:
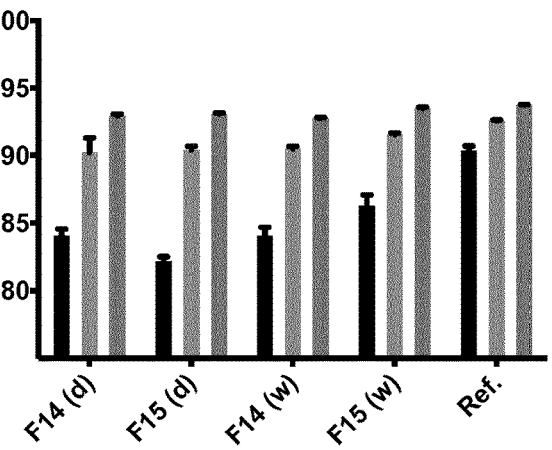

The pellet morphology was measured in terms of AR and sphericity, whereby the fraction 710-1000 μm of MCC-pellets was compared with PVOH formulations after drying (FIG. 2). A mean AR lower or equal to 1.20 was considered as sufficient for pharmaceutical pellets (Krause et al., 2009).

Wet addition of PVOH solution resulted in a lower AR. However, it should be considered that PVOH formulations have a wider range of AR compared to MCC pellets. Therefore, due to the wider range of AR, it was hard to distinguish any influence of drug load or addition of PVOH as dry powder form/solution. Sphericity was less sensitive to detect any differences between formulations. However, all formulations had a high sphericity (>0.85). It's notable that F4, with narrow PSD, complies with a mean AR 1.2 and sphericity >0.9. SEM photographs were used to determine differences in pellet surface morphology (data not shown). In agreement with AR and sphericity, a smooth contour and surface can be observed on these photographs.

The friability (Table 8) was measured in order to determine the mechanical properties of the pellets. Pellets are required to withstand mechanical stress for post-processing steps (e.g. coating, packaging) which could occur for example during coating of pellets.

TABLE 8

Friability (%) (mean ± standard deviation, n = 3 of pellets (710-1.00 mm) as a function of drug load and PVOH/MCC ratio.

| | | Friability % | |
|---|---|---|---|
| | | PVOH dry | PVOH solution |
| 70% DRUG | F2 | 0.10 ± 0.02 | 0.15 ± 0.01 |
| | F3 | 0.39 ± 0.01 | 0.35 ± 0.02 |
| | F4 | 0.18 ± 0.02 | 0.02 ± 0.01 |
| 80% DRUG | F7 | 0.41 ± 0.01 | 0.66 ± 0.03 |
| | F8 | 1.12 ± 0.03 | 0.85 ± 0.04 |
| | F9 | 1.50 ± 0.04 | 0.55 ± 0.01 |
| | F10 | 0.40 ± 0.02 | — |
| 90% DRUG | F12 | 1.35 ± 0.16 | — |
| | F13 | 1.36 ± 0.23 | — |
| | F14 | 3.90 ± 0.20 | 0.35 ± 0.01 |
| | F15 | 0.56 ± 0.07 | 0.17 ± 0.01 |

The friability was slightly higher for pellets with a higher drug load, possibly due to the lower amount of excipients (i.e. PVOH and MCC), which contribute to the mechanical strength of pellets. Furthermore, wet addition of at least 2% PVOH resulted in a lower friability. In literature, different values for friability of pellets, ranging between 1.2 and 3.07%, have been reported (Gazzaniga et al., 1998; Vertommen and Kinget, 1997). All pellets processed with PVOH solution have a friability below 1% for all drug loadings (70-90%), whereby F4 has the lowest friability (0.02±0.01%).

Figure 3:
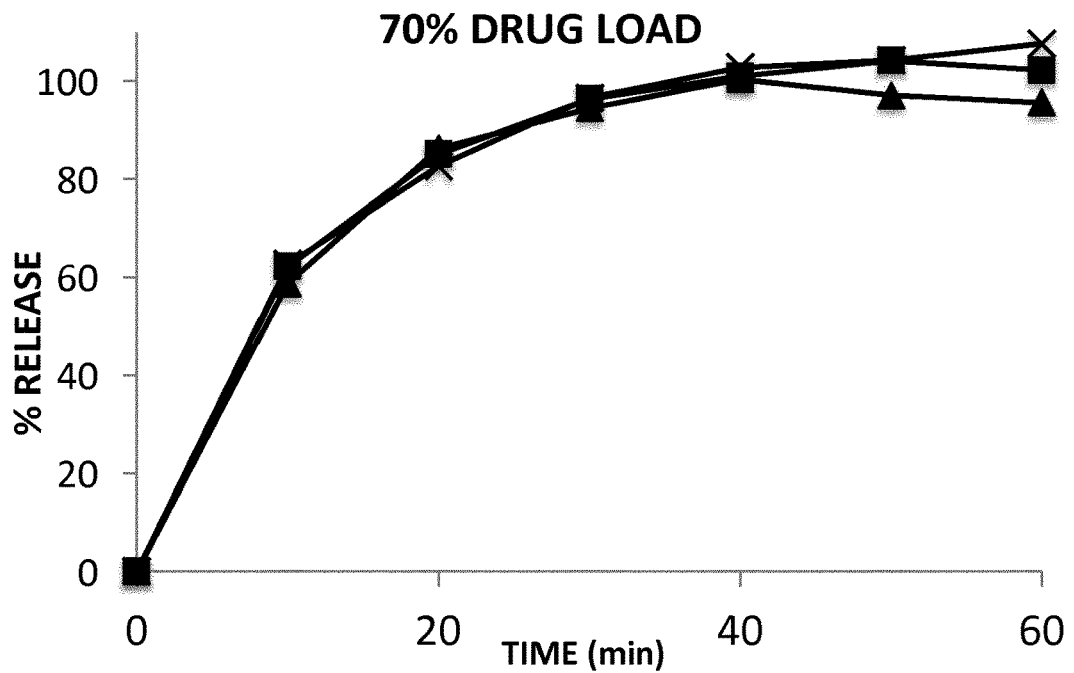
FIG. 3: A. In vitro dissolution profiles (mean±standard deviation, n=3) of pellets with different acetaminophen concentration: Formulations 4, 9 and 14 containing 70%, 80% and 90% drug, respectively. PVOH was added either in dry powder form (■) or as aqueous dispersion (▲). MCC pellets without PVOH containing 50% acetaminophen were used as reference (X). B. Mean in vitro dissolution profiles (±SD, n=3) of metformin.HCl pellets with different coating levels ((■) 0, (▲) 8, (▼) 14 and (●) 20% (w/w)) and (*) Glucophage™ SR 500 (½ tablet) reference.
Figure 3:
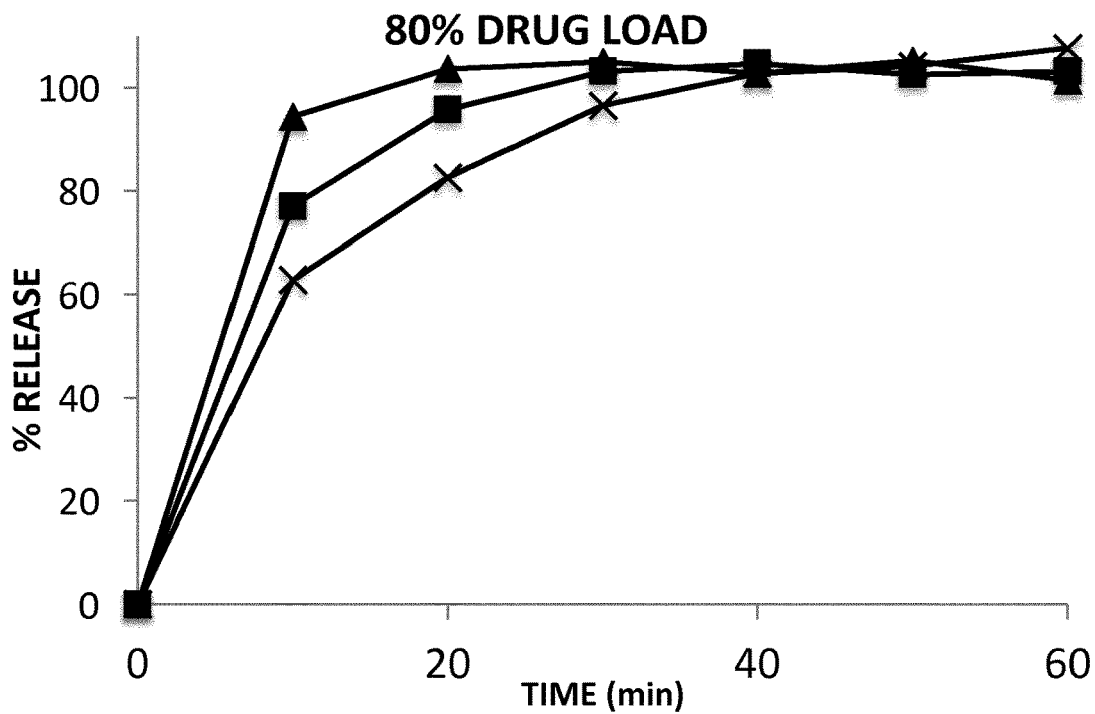

The in vitro dissolution profiles of pellets with different drug load (70-90%) processed with PVOH in dry powder form or solution were compared with MCC pellets (F17) containing a drug load of 50% acetaminophen (FIG. 3). Drug release was mainly dependent on the concentration acetaminophen inside the pellets. Acetaminophen was completely released after 30, 20 and 10 min for pellets containing 70, 80 or 90% acetaminophen, respectively. It is known that MCC pellets do not disintegrate, and therefore release the drug by diffusion (Kranz et al., 2009). However, pellets containing higher drug load were able to disintegrate and thereby release the drug faster. Furthermore, drug release was independent of PVOH addition method, since no difference was observed between formulation containing PVOH as dry powder form and formulations containing PVOH solution.

All tested PVOH grades (Table 3) could enhance the extrusion-spheronisation properties of the wet mass. Despite, more stickiness to the friction plate was observed in case higher molecular weights were used. This phenomenon was not observed when lower molecular weight PVOH grades (e.g. PVA505, PVA4-88, PVA5-88 and PVA18-88) were used. Stickiness to the friction plate could be partially countered by adding less water. Although, more shark skinning and extrudate brittleness was found in case less water was added.

Especially partially (including low) hydrolysed PVOH grades are interesting extrusion-spheronisation aids because of their high aqueous solubility. Based on their high solubility in water, they can be easily added via the wet addition method. All low and partially hydrolysed PVOH grades could enhance the extrusion-spheronisation properties of the wet mass. The range of water concentration was found more narrow with increasing PVOH molecular weight.

2.2 Evaluation of PVOH as Pelletisation Aid for the Production of Fixed Dose Combination (Acetaminophen/Tramadol.HCl)

In the second part of this study, the use of pellets with PVOH as pelletisation aid in fixed dose combinations was evaluated. Fixed dose combinations consist out of 2 or more drugs that are combined inside the pellet and thus requires pellets which could contain a high drug concentration. F4, which contains 70% acetaminophen, 6% PVOH and 24% MCC, was the most promising formulation with a narrow PSD (low span index), mean AR 1.2, sphericity >0.9 and friability <1%. This formulation was transformed to a fixed dose combination of acetaminophen/tramadol.HCl (325/37.5) (Table 9).

TABLE 9

Composition of pellet formulation containing acetaminophen and acetaminophen/tramadol.

| Concentration (%) | Acetaminophen | Acetaminophen/Tramadol•HCl |
|---|---|---|
| Acetaminophen | 70 | 62.8 |
| Tramadol•HCl | — | 7.2 |
| PVOH | 6 | 6 |
| MCC | 24 | 24 |
| Water content (%)* | 38.3 | 35 |

*Water content was calculated as a percentage of the total dry weight of each formulation The optimal water content of formulations containing acetaminophen/tramadol.HCl was slightly lower compared to acetaminophen formulation, since the aqueous solubility of tramadol (30-100 mg/ml) (Sudha et al., 2010) was higher compared to acetaminophen (14.3 mg/ml) (Kalantzi et al., 2006). This confirms that drug solubility influences the required amount of water for the production of pellets (Verheyen et al., 2009). The span of formulations containing acetaminophen and acetaminophen/tramadol.HCl were compared with reference pellets without acetaminophen (F16) (Table 10).

TABLE 10

Particle size data ($D_{10}$, $D_{50}$, $D_{90}$ and span) (mean ± standard deviation, n = 3) of formulations containing acetaminophen or acetaminophen/tramadol•HCl (62.8/7.2). MCC pellets were used as reference. The significance of the results between formulations was determined with an independent sample t-test. Span values) with different superscripts are different at the 0.05 level of significance compared to MCC (n = 3).

| Formulation | $D_{10}$ | $D_{50}$ | $D_{90}$ | Span ($d_{90}$-$d_{10}$) |
|---|---|---|---|---|
| Acetaminophen | 804.1 ± 57.0 | 1054.1 ± 26.6 | 1271.4 ± 29.5 | 467 ± 32[a] |
| Acetaminophen/Tramadol•HCl | 1071.1 ± 99.5 | 1723.2 ± 148.2 | 2060.4 ± 182.9 | 989 ± 88[b] |
| MCC | 663.3 ± 24.2 | 888.0 ± 11.1 | 1097.5 ± 6.2 | 434 ± 19[a] |

A significant difference ($p<0.05$) in span was observed between reference (MCC) or acetaminophen pellets and pellets containing acetaminophen/tramadol.HCl, whereby the latter formulation had a broader PSD. Furthermore, pellet sizes ($D_{10}$, $D_{50}$, $D_{90}$) of formulations with acetaminophen/tramadol.HCl were increased, possibly due to an increased solubility of tramadol.HCl, and thus decreasing solid content of the formulation for the same PVOH concentration. An increased binder concentration (i.e. PVOH) inside the formulation results into the formation of larger pellets (Garekani et al., 2013).

Figure 4:
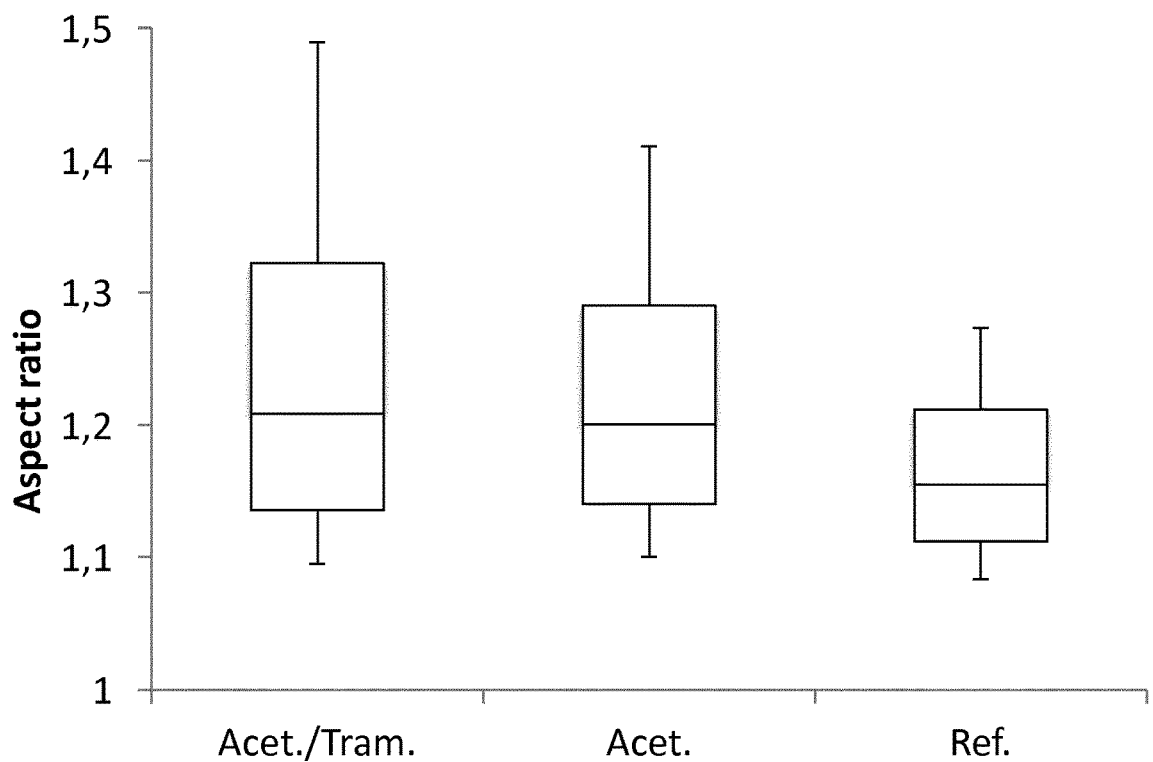
FIG. 4: Aspect ratio (AR) and sphericity (mean±standard deviation, n=3) of formulations containing 70% drug. Acetaminophen (Acet.) or an acetaminophen/tramadol.HCl mixture (62.8/7.2) (Acet./Tram.) was included as drug in the pellets. MCC pellets without drug were used as reference (Ref.). The 710-1000 μm sieve fraction was used for analysis (n=3).
Figure 4:
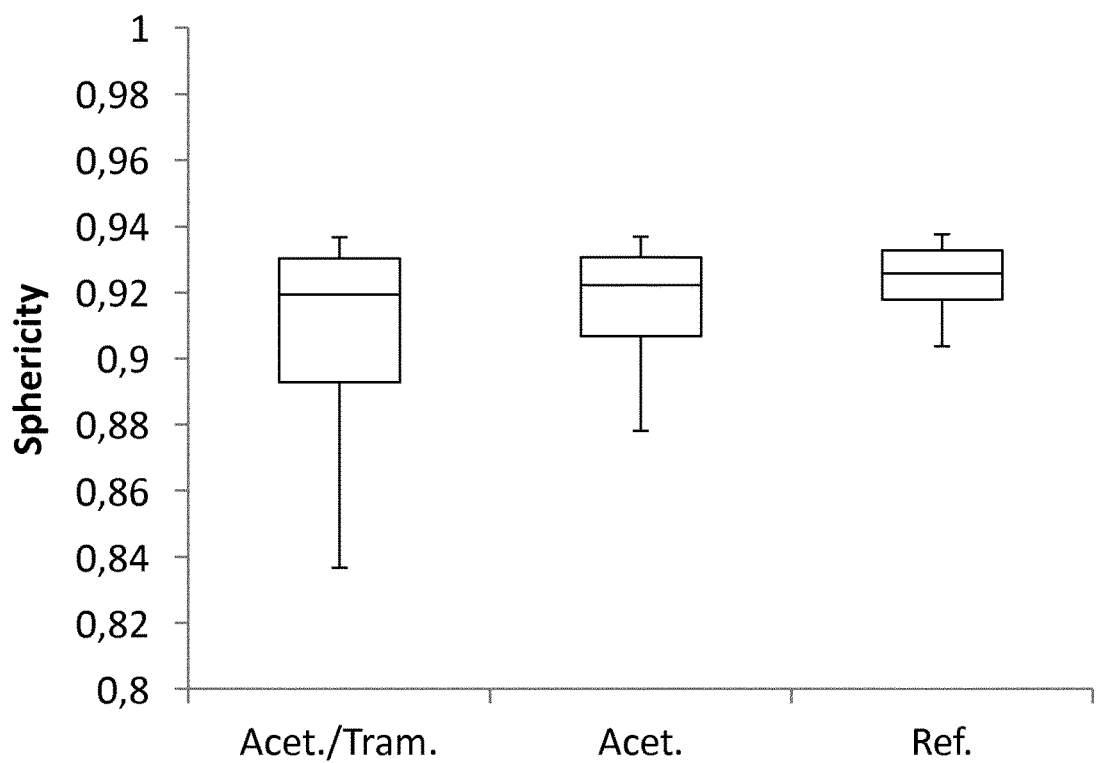

Pellet morphology was evaluated by means of AR and sphericity (FIG. 4), whereby AR was slightly higher for pellets containing acetaminophen/tramadol.HCl. The mean AR (1.21) was marginally above 1.2 which is required for pharmaceutical applications (Krause et al., 2009). A wider distribution for sphericity was detected with a high mean value of 0.92.

Figure 5:
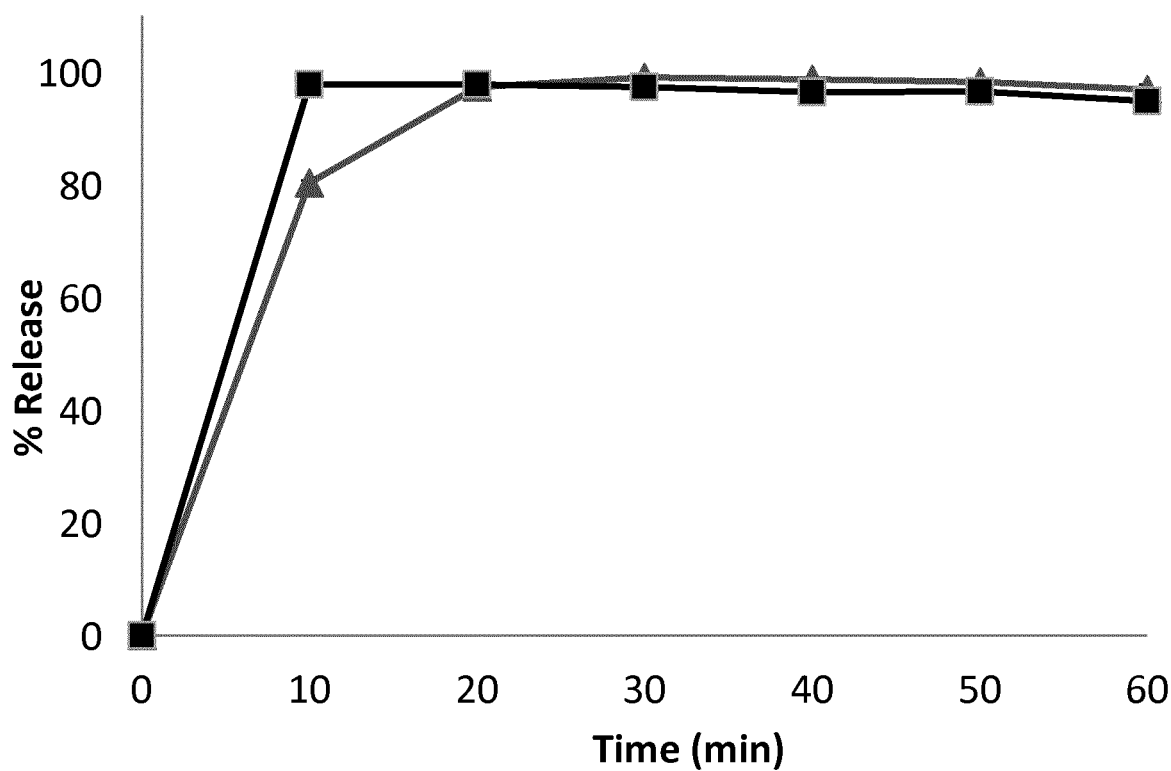
FIG. 5: In vitro dissolution profiles (mean±standard deviation, n=3) of acetaminophen (▲) and tramadol.HCl (■) from acetaminophen/tramadol.HCl pellets.

Friability of both formulations was low as for formulations containing acetaminophen and acetaminophen/tramadol.HCl respectively 0.02±0.01% and 0.14±0.01, was obtained. FIG. 5 shows the in vitro dissolution profiles of fixed dose combination pellets with acetaminophen/tramadol.HCl (325/37.5).

Tramadol.HCl was released quickly within 10 min., whereas acetaminophen was released within min. It was noticed that acetaminophen release was faster inside acetaminophen/tramadol.HCl pellets compared to pellets containing 70% acetaminophen. This could be explained due to the addition of tramadol.HCl, which has a high solubility that contributes to a faster disintegration of the pellet.

2.3 Coating

Usually, the drug load of sustained release pellets for highly water soluble drugs is limited as large amounts of MCC (to enable extrusion-spheronisation) and release retarding polymer are needed. As the MCC concentration could be lowered by the addition of PVOH, high quality pellets could be obtained with a metformin load up to 90%.

lution testing, the morphology of the 20% coated pellets remained unchanged. For the Glucophage™ SR tablet (Merck Serono), a gel-like layer was formed around the matrix tablet due to the hydration of hydroxypropylmethylcellulose and sodium carboxymethylcellulose which are incorporated as release retarding agents.

2.4 Taste Masking

As the MCC concentration could be lowered by the addition of PVOH, high drug loaded taste masked ibuprofen pellets were successfully manufactured via extrusion-spheronisation whereby the bitter taste of high drug loaded ibuprofen pellets completely disappeared after coating. The effectiveness of the coating was evaluated in healthy volunteers.

2.5 In Vivo

For the pellet formulation, a maximum plasma level of 2.5 µg/mL was reached 3.5 h ($T_{max}$) post administration. In case of Glucophage™ SR (½ tablet), a $C_{max}$ value of 2.4 µg/mL was observed 2.8 h ($T_{max}$) after oral intake. The $HVD_{T50\%\ Cmax}$ values were 5.1 and 5.6 h, resulting in $R_D$ values of 1.6 and 1.7 for the pellets and Glucophage™ SR reference formulations, respectively. Despite the narrow absorption range (i.e. mainly upper part of gastro-intestinal tract) of metformin hydrochloride and shorter gastro-intestinal residence time of multiparticulate dosage forms, the pellet and tablet formulations did not have significantly different pharmacokinetic parameters (i.e. AUC, $T_{max}$, $C_{max}$, $HVD_{t50\%\ Cmax}$ and $R_D$). An observation that could be explained by the higher sensitivity of the hydrated gel layer (at the surface of the Glucophage tablets) to gastrointestinal shear forces. This hypothesis was confirmed after in vivo experiments as no residue of the reference tablet could be detected in the faeces. In contrast, the geometric shape of the pellets (which had no residual drug content) was unaffected.

TABLE 11

Mean pharmacokinetic parameters (±SD, n = 6) after oral administration of 250 mg metformin•HCl to dogs as pellets and Glucophage ™ SR 500 (1/2 tablet). According to independent sample t-testing, both formulations did not significantly differ.

| Formulation | $C_{max}$ (µg/mL) | $T_{max}$ (h) | $AUC_{0-12h}$ (µg · h/mL) | $HVD_{t50\%Cmax}$ (h) | $R_D$ |
|---|---|---|---|---|---|
| pellets | 2.5 ± 0.2 | 3.5 ± 1.0 | 14.5 ± 2.4 | 5.1 ± 1.4 | 1.6 ± 0.4 |
| Glucophage ™ SR | 2.4 ± 0.2 | 2.8 ± 0.4 | 15.0 ± 0.9 | 5.6 ± 0.6 | 1.7 ± 0.2 |

Figure 6:
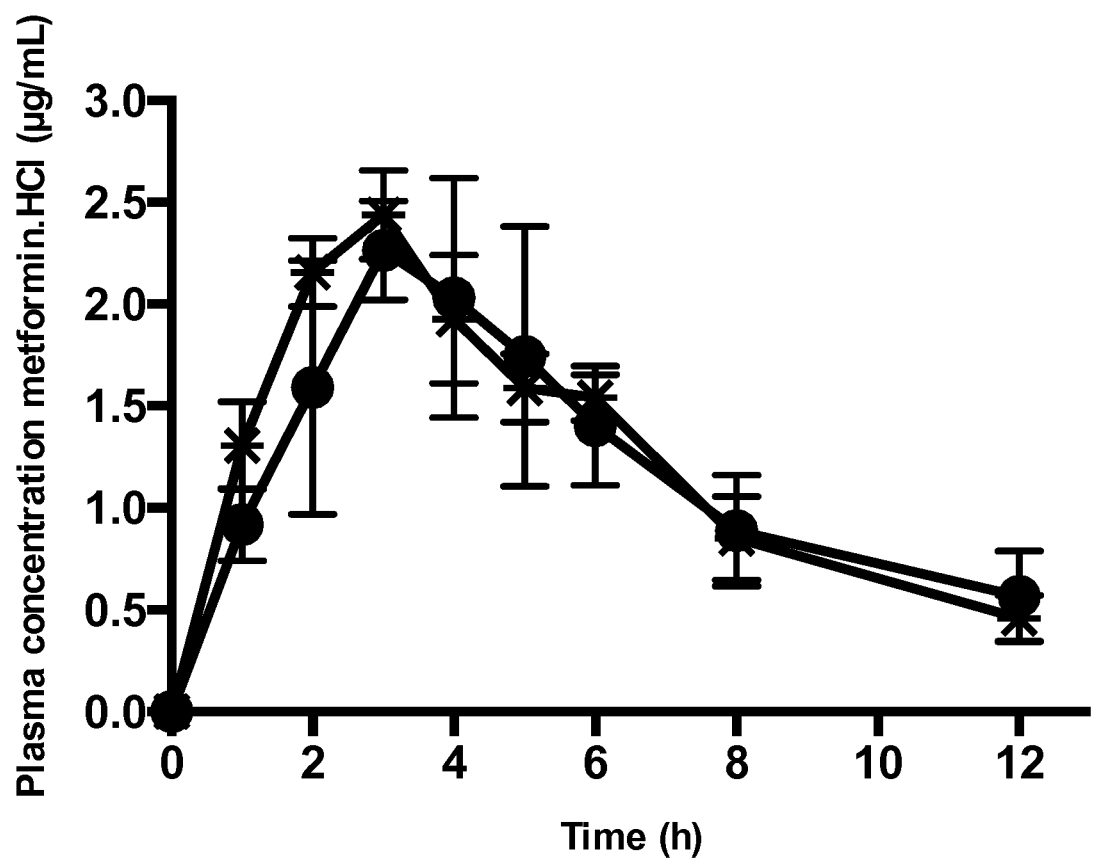
FIG. 6: Mean plasma concentration-time profiles (±SD, n=6) after oral administration of 250 mg Metformin.HCl to beagle dogs: (●) coated PVA pellets (F24) and (*) Glucophage™ SR 500 (½ tablet).

Based on its high drug content and low friability (0.66±0.03%), formulation 20 (F20) was selected for coating trials. Different coating levels were applied (Table 4) and the influence on drug release was plotted as a function of dissolution time. As shown in FIG. 3. (B), release kinetics decreased in function of coating thickness. Moreover, it was found that a 20% (w/w) coating (percentage based on pellet weight) was able to sustain drug release for 12 h. When coating experiments were performed with an aqueous solution, the drug on the pellet surface dissolved faster. Therefore, it was able to diffuse into the polymer film during coating trials and act as a pore-forming agent during dissolution testing. This is reduced by using sufficient coating material (>15-20%) or by pre-treating the pellets with talc. The influence of dissolution testing on pellet morphology (i.e. surface porosity) was examined via SEM on coated and uncoated pellets (results not shown). Whereas the surface porosity of the uncoated pellets increased after 12 h disso- PVOH pellets were successfully coated with an acrylic-based sustained release polymer, sustaining drug release from pellets containing 70% (w/w) metformin hydrochloride over a period of 12 h. After oral administration the in vivo performance of the coated pellets did not significantly differ from the commercially available Glucophage™ SR reference formulation (FIG. 6).

3 CONCLUSIONS

This study demonstrates that PVOH solution is a promising pelletisation aid for the production of granules/pellets with high drug concentration (up to 70-90%), since MCC based pellets could only be processed with satisfactory properties and yield up to a concentration of 50% acetaminophen. Subsequently, those high drug loaded pellets (on the basis of PVOH) were used to produce a fixed dose combination of acetaminophen/tramadol.HCl, whereby although pellet quality (span, AR, sphericity and friability) was slightly decreased, in vitro dissolution profiles of pellets containing acetaminophen/tramadol.HCl showed a fast drug release. In addition, the PVOH pellets were successfully coated thereby sustaining drug release or masking taste. After oral administration, the in vivo performance of the coated pellets did not significantly differ from the commercially available formulation.

REFERENCES

Cesar A. de Araújo-Júnior, Fernanda S. de Oliveira Costa, Stephania F. Taveira, Ricardo N. Marreto, Marize C. Valadares, Eliana M. Lima, Preparation of pellets containing Pothomorphe umbellata extracts by extrusion-spheronization: improvement of 4-nerolidylcatechol photostability, Revista Brasileira de Farmacognosia, Volume 23, Issue 1, January-February 2013, Pages 169-174.

Basit, A. W., Newton, J. M., Lacey, L. F., 1999. Formulation of ranitidine pellets by extrusion-spheronization with little or no microcrystalline cellulose. Pharm Dev Technol 4, 499-505.

Chatchawalsaisin, J., Podczeck, F., Newton, J. M., 2005. The preparation by extrusion/spheronization and the properties of pellets containing drugs, microcrystalline cellulose and glyceryl monostearate. Eur J Pharm Sci 24, 35-48.

Chatlapalli, R., Rohera, B. D., 1998. Physical characterization of HPMC and HEC and investigation of their use as pelletization aids. Int J Pharmaceut 161, 179-193.

De Jaeghere W, De Beer T, Van Bocxlaer J, Remon J P, Vervaet C. Hot-melt extrusion of polyvinyl alcohol for oral immediate release applications. Int J Pharm. 2015 Aug. 15; 492(1-2):1-9.

Dukic-Ott, A., Remon, J. P., Foreman, P., Vervaet, C., 2007. Immediate release of poorly soluble drugs from starch-based pellets prepared via extrusion/spheronisation. Eur J Pharm Biopharm 67, 715-724.

Dukic-Ott, A., Thommes, M., Remon, J. P., Kleinebudde, P., Vervaet, C., 2009. Production of pellets via extrusion-spheronisation without the incorporation of microcrystalline cellulose: A critical review. Eur J Pharm Biopharm 71, 38-46.

Fielden, K. E., Newton, J. M., Obrien, P., Rowe, R. C., 1988. Thermal Studies on the Interaction of Water and Microcrystalline Cellulose. J Pharm Pharmacol 40, 674-678.

Gabr, R. Q., Padwal, R. S., Brooks, D. R., 2010. Determination of metformin in human plasma and urine by high-performance liquid chromatography using small sample volume and conventional octadecyl silane column. J Pharm Sci. 13, 486-494.

Garekani, H. A., Nokhodchi, A., Rayeni, M. A., Sadeghi, F., 2013. Preparation and characterization and release properties of Eudragit RS based ibuprofen pellets prepared by extrusion spheronization: effect of binder type and concentration. Drug Dev Ind Pharm 39, 1238-1246.

Gazzaniga, A., Sangalli, M. E., Bruni, G., Zema, L., Vecchio, C., Giordano, F., 1998. The use of beta-cyclodextrin as a pelletization agent in the extrusion/spheronization process. Drug Dev Ind Pharm 24, 869-873.

Kalantzi, L., Reppas, C., Dressman, J. B., Amidon, G. L., Junginger, H. E., Midha, K. K., Shah, V. P., Stavchansky, S. A., Barends, D. M., 2006. Biowaiver monographs for immediate release solid oral dosage forms: Acetaminophen (Paracetamol)—Commentary. J Pharm Sci-Us 95, 4-14.

Koester, M., Thommes, M., 2010. New Insights into the Pelletization Mechanism by Extrusion/Spheronization. Aaps Pharmscitech 11, 1549-1551.

Kooiman, K., Bohmer, M. R., Emmer, M., Vos, H. J., Chlon, C., Shi, W. T., Hall, C. S., de Winter, S. H. P. M., Schroen, K., Versluis, M., de Jong, N., van Wamel, A., 2009. Oil-filled polymer microcapsules for ultrasound-mediated delivery of lipophilic drugs. J Control Release 133, 109-118.

Kranz, H., Jurgens, K., Pinier, M., Siepmann, J., 2009. Drug release from MCC- and carrageenan-based pellets: Experiment and theory. Eur J Pharm Biopharm 73, 302-309.

Krause, J., Thommes, M., Breitkreutz, J., 2009. Immediate release pellets with lipid binders obtained by solvent-free cold extrusion. Eur J Pharm Biopharm 71, 138-144.

Law, M. F. L., Deasy, P. B., 1998. Use of hydrophilic polymers with microcrystalline cellulose to improve extrusion-spheronization. Eur J Pharm Biopharm 45, 57-65.

Lustig-Gustafsson, C., Johal, H. K., Podczeck, F., Newton, J. M., 1999. The influence of water content and drug solubility on the formulation of pellets by extrusion and spheronisation. Eur J Pharm Sci 8, 147-152.

Mallipeddi, R., Saripella, K. K., Neau, S. H., 2010. Use of coarse ethylcellulose and PEO in beads produced by extrusion-spheronization. Int J Pharmaceut 385, 53-65.

Meier, J., Nüesch, E., Schmidt, R., 1974. Pharmacokinetic criteria for the evaluation of retard formulations. Europ J Clin Pharmacol. 7 (6), 429-432.

Gabrielsson, J., Weiner, D., 2000. Pharmacokinetic and Pharmacodynamic Data Analysis: concepts and applications. 3rd edition. Swedish Pharmaceutical Press. Stockholm, Sweden, ISBN 91 8627 492 9.

Lalloo, A. K., McConnell, E. L., Jin, L., Elkes, R., Seiler, C., Wu, Y., 2012. Decoupling the role of image size and calorie intake on gastric retention of swelling-based gastric retentive formulations: Pre-screening in the dog model. Int J Pharm. 431, 90-100.

Oconnor, R. E., Schwartz, J. B., 1985. Spheronization 0.2. Drug Release from Drug-Diluent Mixtures. Drug Dev Ind Pharm 11, 1837-1857.

Raffa, R. B., 2001. Pharmacology of oral combination analgesics: rational therapy for pain. J Clin Pharm Ther 26, 257-264.

Sudha, B. S., Sridhar, B. K., Srinatha, A., 2010. Modulation of Tramadol Release from a Hydrophobic Matrix: Implications of Formulations and Processing Variables. Aaps Pharmscitech 11, 433-440.

Swarbrick, J. S., 2006. Encyclopedia of Pharmaceutical Technology, Third Edition—6 Volume Set. Taylor & Francis.

Verheyen, P., Steffens, K. J., Kleinebudde, P., 2009. Use of crospovidone as pelletization aid as alternative to microcrystalline cellulose: effects on pellet properties. Drug Dev Ind Pharm 35, 1325-1332.

Vertommen, J., Kinget, R., 1997. The influence of five selected processing and formulation variables on the particle size, particle size distribution, and friability of pellets produced in a rotary processor. Drug Dev Ind Pharm 23, 39-46.

Wlosnewski, J. C., Kumpugdee-Vollrath, M., Sriamornsak, P., 2010. Effect of drying technique and disintegrant on physical properties and drug release behavior of microcrystalline cellulose-based pellets prepared by extrusion/spheronization. Chem Eng Res Des 88, 100-108.

Yu, W. L., Hancock, B. C., 2008. Evaluation of dynamic image analysis for characterizing pharmaceutical excipient particles. Int J Pharmaceut 361, 150-157.

The invention claimed is:

1. A pharmaceutical dosage form comprising one or more pellets having a core and a coating, wherein said core comprises at least 40% by weight active agent, from 1% to 15% by weight of partially hydrolyzed polyvinylalcohol (PVOH) with a degree of hydrolysis from about 70% to about 95%, and from 0.5% to 35% by weight microcrystalline cellulose (MCC).

2. The pharmaceutical dosage form according to claim 1, wherein the PVOH/MCC ratio in the core of the pellet is from 50/50 to 5/95.

3. The pharmaceutical dosage form according to claim 1, wherein the core comprises at least two active agents.

4. The pharmaceutical dosage form according to claim 1, wherein said one or more pellets are prepared by an extrusion and spheronization process.

5. The pharmaceutical dosage form according to claim 1, wherein said pellet is an extrudate.

6. The pharmaceutical dosage form according to claim 1, wherein said pellet is a cold extrudate.

7. The pharmaceutical dosage form according to claim 1, wherein said pellets have diameters from about 0.3 mm to about 3 mm.

8. The pharmaceutical dosage form according to claim 1, wherein said dosage form is formulated as a multiparticulate and/or oral dosage form.

9. The pharmaceutical dosage form according to claim 1, wherein the active agent is an antidiabetic agent.

10. The pharmaceutical dosage form according to claim 1, wherein the active agent is metformin.

11. The pharmaceutical dosage form according to claim 1, wherein the coating when present comprises a taste masking agent.

12. A tablet, capsule or unit-dose comprising a multiplicity of the pellets as defined in claim 1.

* * * * *